United States Patent
Säll

US 11,235,103 B2
Feb. 1, 2022

(54) MEDICAMENT DELIVERY DEVICE

(71) Applicant: SHL MEDICAL AG, Zug (CH)

(72) Inventor: Daniel Säll, Segeltorp (SE)

(73) Assignee: SHL MEDICAL AG, Zug (CH)

( * ) Notice: Subject to any disclaimer, the term of this patent is extended or adjusted under 35 U.S.C. 154(b) by 180 days.

(21) Appl. No.: 16/477,838

(22) PCT Filed: Dec. 28, 2017

(86) PCT No.: PCT/EP2017/084771
§ 371 (c)(1),
(2) Date: Jul. 12, 2019

(87) PCT Pub. No.: WO2018/134034
PCT Pub. Date: Jul. 26, 2018

(65) Prior Publication Data
US 2019/0365999 A1  Dec. 5, 2019

(30) Foreign Application Priority Data
Jan. 17, 2017 (EP) .................................. 17151735

(51) Int. Cl.
A61M 5/20 (2006.01)
A61M 5/31 (2006.01)
A61M 5/32 (2006.01)

(52) U.S. Cl.
CPC ........ *A61M 5/2033* (2013.01); *A61M 5/3146* (2013.01); *A61M 5/3204* (2013.01);
(Continued)

(58) Field of Classification Search
CPC ............ A61M 5/20; A61M 5/31; A61M 5/32; A61M 5/3146; A61M 5/2033;
(Continued)

(56) References Cited

U.S. PATENT DOCUMENTS

2011/0009821 A1*  1/2011 Jespersen ............ A61M 5/1452
604/135
2012/0211005 A1  8/2012 Bauer et al.

FOREIGN PATENT DOCUMENTS

CN  1302213 A  7/2001
CN  1505534 A  6/2004
(Continued)

OTHER PUBLICATIONS

International Search Report and Written Opinion for Int. App. No. PCT/EP2017/084771, dated Mar. 19, 2018.

*Primary Examiner* — Bhisma Mehta
*Assistant Examiner* — Neeraja Gollamudi
(74) *Attorney, Agent, or Firm* — McDonnell Boehnen Hulbert & Berghoff LLP

(57) ABSTRACT

A medicament delivery device is presented having a housing configured to accommodate a medicament container filled with medicament, a drive unit comprising a plunger rod operable to act on the medicament container, a mechanical activation mechanism configured to interact with the drive unit, where the mechanical activation mechanism is movable between certain predetermined states when interacting with the drive unit, a recording unit capable of recording status changes of the medicament delivery device including the status of the mechanical activation mechanism, and detection elements operably connected to the recording unit and positioned such as to detect when the activation mechanism has been moved between certain predetermined states.

10 Claims, 22 Drawing Sheets

(52) U.S. Cl.
CPC .............. *A61M 2005/208* (2013.01); *A61M 2005/2013* (2013.01); *A61M 2205/215* (2013.01)

(58) Field of Classification Search
CPC .......... A61M 5/3204; A61M 2205/215; A61M 2005/2013; A61M 2005/208
See application file for complete search history.

(56) References Cited

FOREIGN PATENT DOCUMENTS

| | | | | |
|---|---|---|---|---|
| CN | 101304775 | A | 11/2008 | |
| CN | 104080501 | A | 10/2014 | |
| CN | 104246782 | A | 12/2014 | |
| EP | 1349596 | A1 * | 10/2003 | ........ A61M 5/14244 |
| EP | 1349596 | A1 | 10/2003 | |
| TW | 201336538 | A | 9/2013 | |
| WO | 2004/028598 | A1 | 4/2004 | |
| WO | 2009/035761 | A2 | 3/2009 | |
| WO | WO-2010098931 | A * | 9/2010 | .............. A61M 5/24 |
| WO | 2011/126439 | A1 | 10/2011 | |
| WO | WO-2011126439 | A1 * | 10/2011 | .......... A61M 5/3146 |
| WO | 2013/089616 | A1 | 6/2013 | |
| WO | 2016/180873 | A1 | 11/2016 | |
| WO | 2016/193229 | A1 | 12/2016 | |

\* cited by examiner

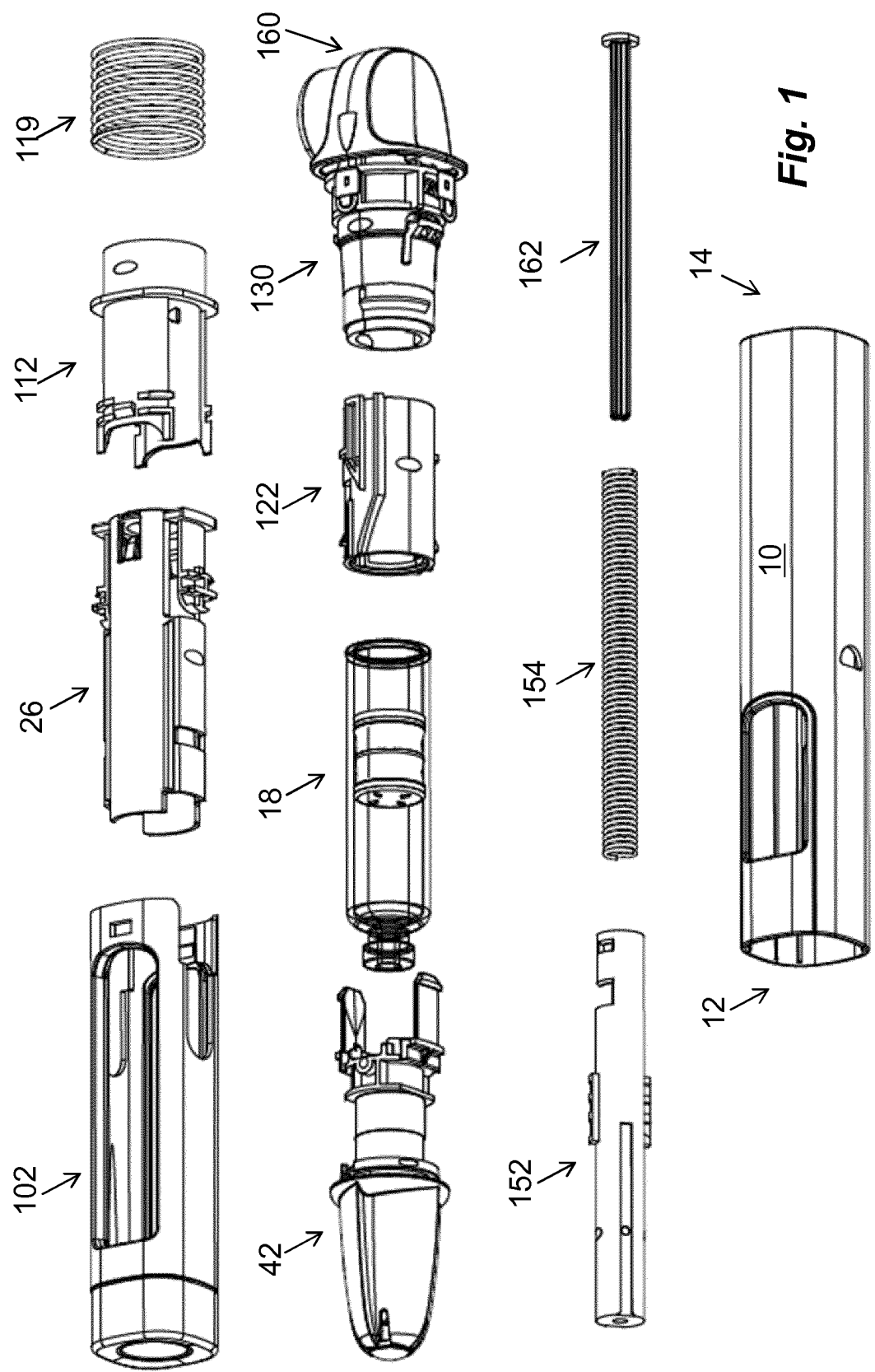

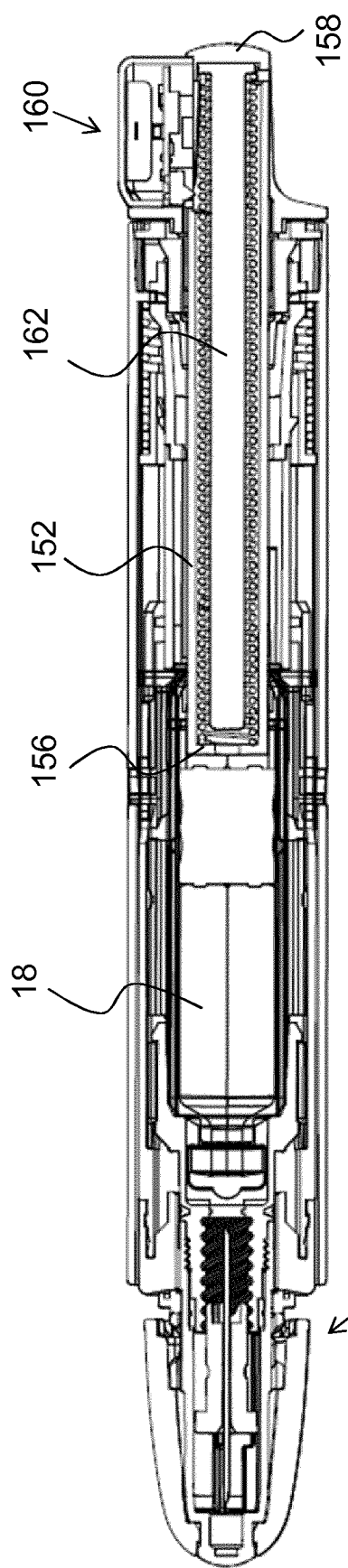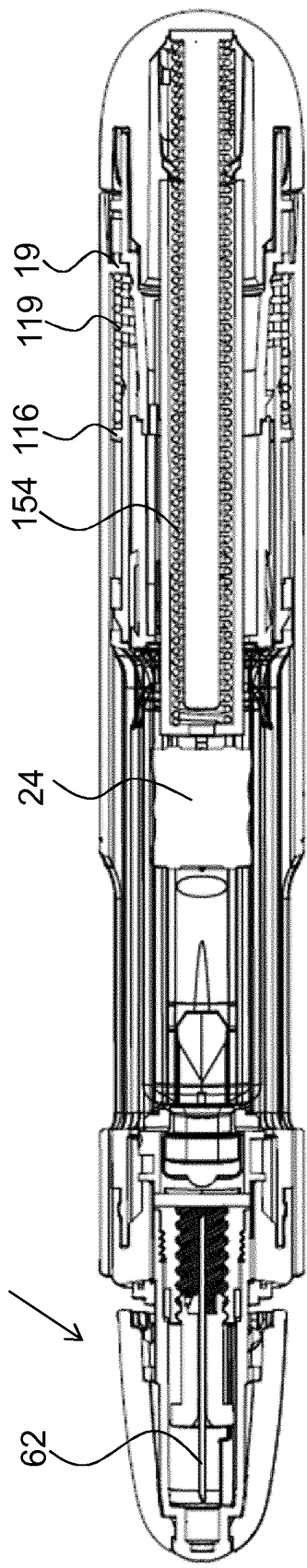
Fig. 2a
Fig. 2b

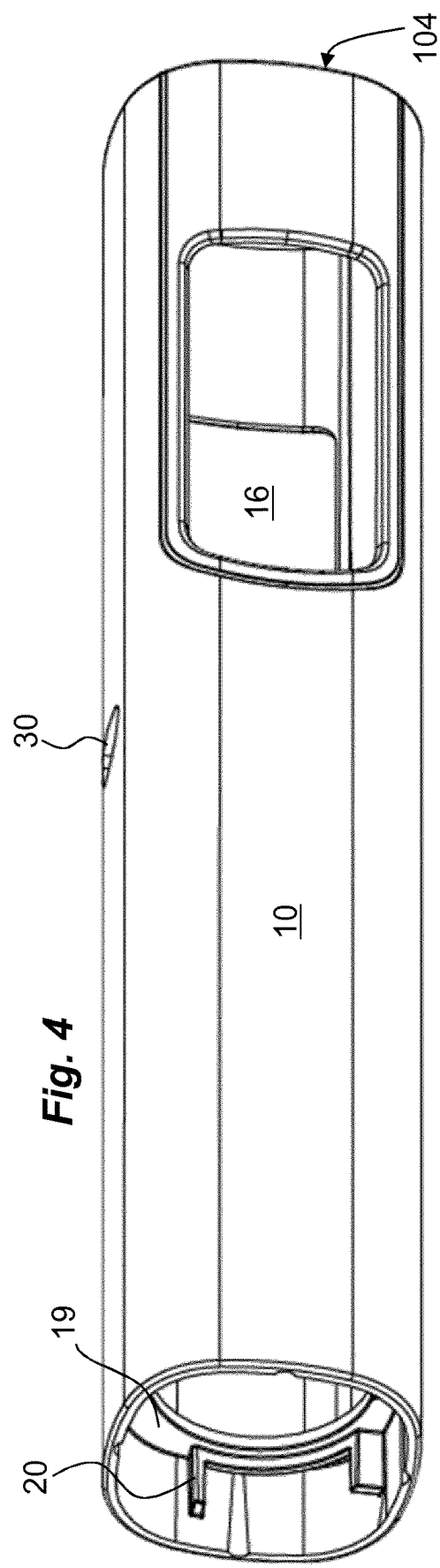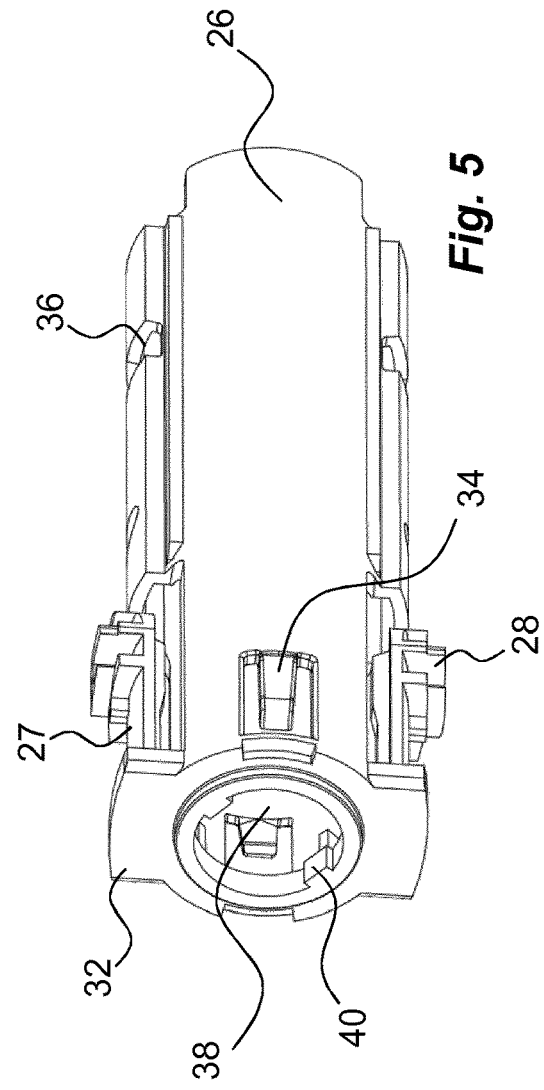

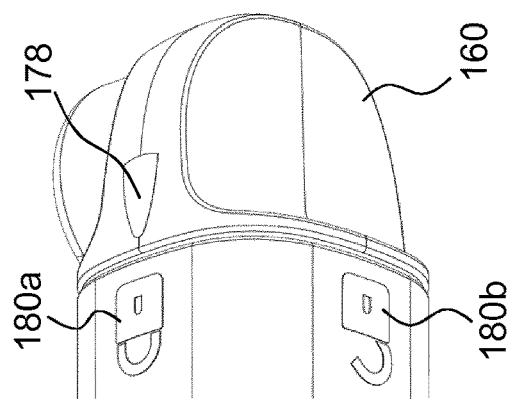
*Fig. 12*
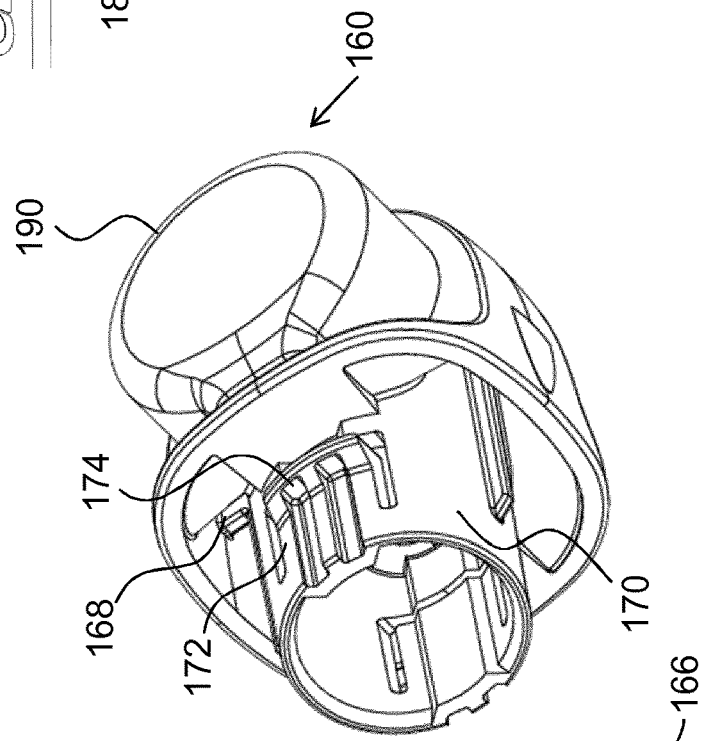
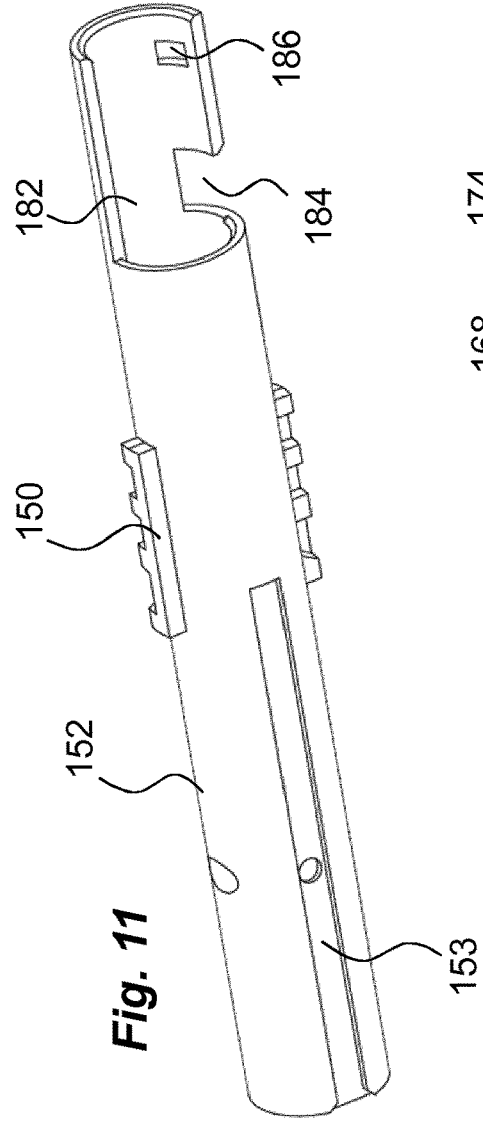
*Fig. 11*
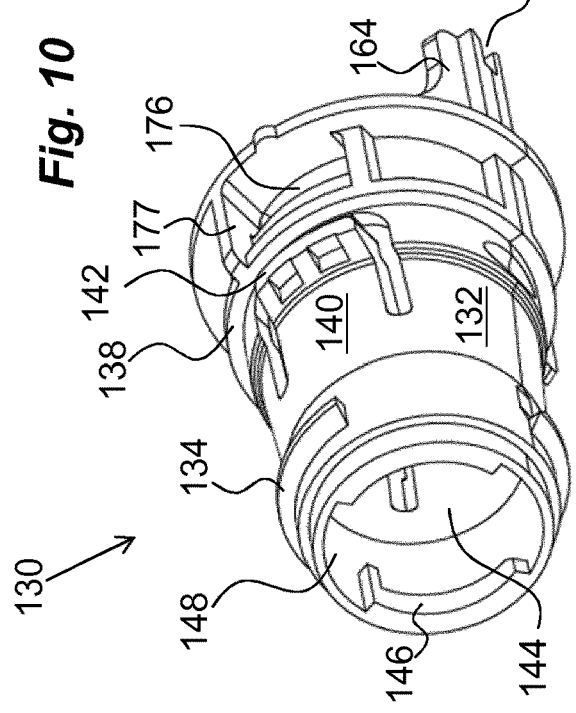
*Fig. 10*

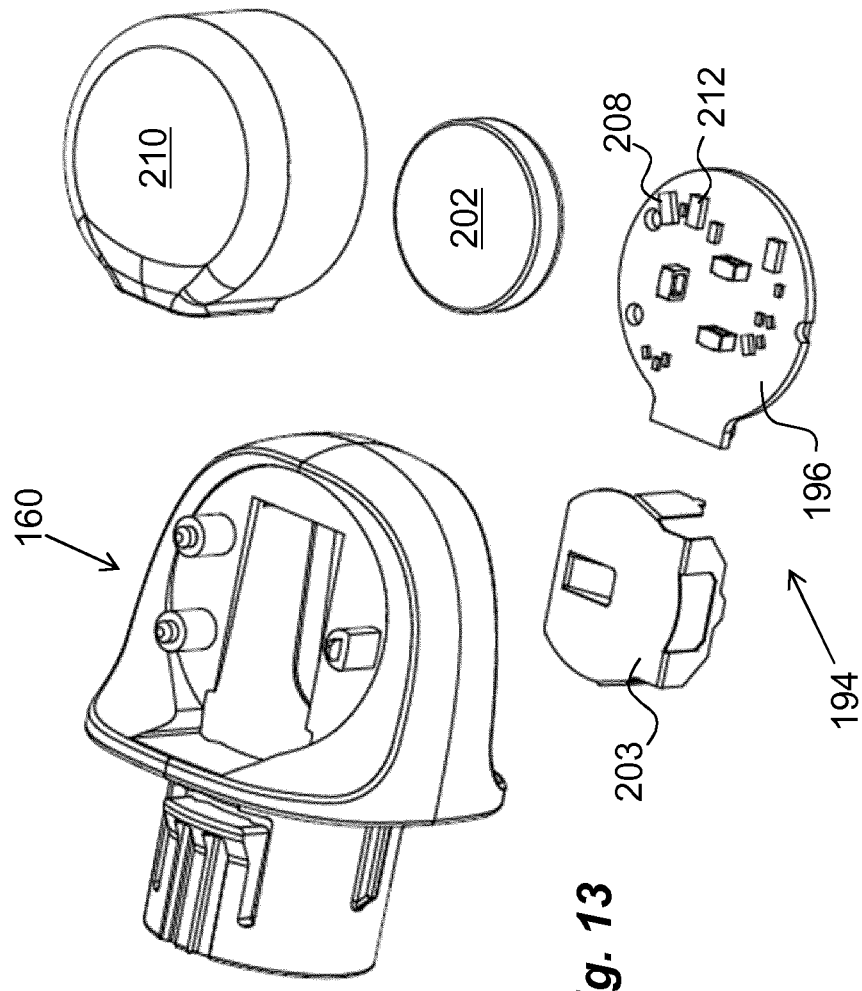
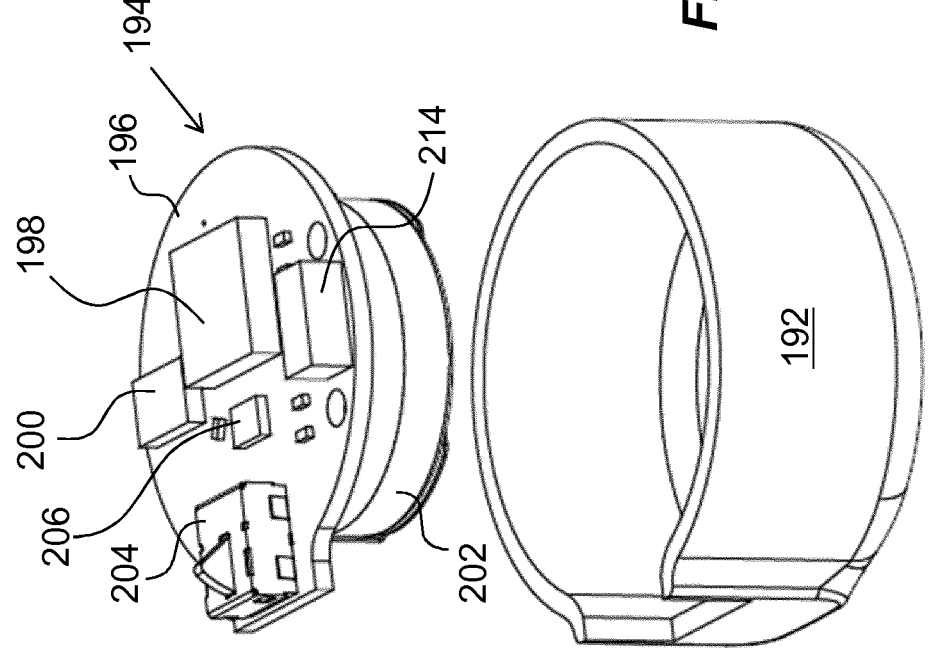
Fig. 13

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2017/084771 filed Dec. 28, 2017, which claims priority to European Patent Application No. 17151735.2 filed Jan. 17, 2017. The entire disclosure contents of these applications are herewith incorporated by reference into the present application.

TECHNICAL AREA

The present disclosure relates to a medicament delivery device provided with connectivity functions.

BACKGROUND

More and more medicament delivery devices are nowadays being provided with functionality that will enable the monitoring and recording of different status changes of the devices when used by the users themselves. The monitoring and recording features will then provide healthcare staff with information on how the patient is handling the administration of the medicaments prescribed. Also patients themselves may benefit from the monitoring features, providing a help of remembering and an aid of alerting when a medicament delivery occurrence is scheduled.

One problem with a few medicament delivery devices that are provided with such functionality is how and when to activate the recording units. One medicament delivery device is disclosed in document US 2012/0211005 having a plurality of different solutions for activating and monitoring of the medicament delivery device. As example, a start button may be arranged, which is manually depressed in order to activate the medicament delivery device. On the other hand, the medicament delivery device may be activated by a proximity sensor. When the device is activated it may perform a number of activities such as audio information on how the medicament delivery device is to be handled and positioned when delivering a dose of medicament. Further sensors are arranged to detect changes of status of the medicament delivery device during and after use. The medicament delivery device can further comprise a network interface device for wireless communication with external sources. The medicament delivery device of US 2012/0211005 is in all a rather complicated and power consuming medicament delivery device that will not likely be very easy for an unskilled person to use. Further the power consumption will likely be rather high, whereby at least three button cells are required.

There is thus room for medicament delivery devices provided with additional functions such as monitoring and recording functions that are easy and simple for unexperienced users, and that do not consume large amounts of power when used.

SUMMARY

In the present application, the term "distal part/end" refers to the part/end of the device, or the parts/ends of the members thereof, which under use of the device, is located the furthest away from a delivery site of a patient. Correspondingly, the term "proximal part/end" refers to the part/end of the device, or the parts/ends of the members thereof, which under use of the device is located closest to the delivery site of the patient.

In the following description, the term "smart devices" will be used. In this context, smart devices may include electronic devices that are provided with processors that are capable of running computer programs, as well as comprising storage space to store programs and data retrieved from different external sources. It is further to be understood that the smart devices are provided with communication systems that are capable of communicating with data networks in order to access different databases. It is to be understood that databases may be accessed via the internet, so called cloud services, and/or databases that are connected directly to and accessed via local area networks. It is further to be understood that the smart devices in this context comprise some sort of human-machine interface for two-way communication. The human-machine interface may comprise displays, keyboards, microphones, loudspeakers, I/O-ports for connection of peripherals. Further, the smart devices may be provided with antennas for wireless communication with the networks. Also, the smart devices may be arranged with receiving and transmitting mechanisms capable of communicating with RFID/NFC tags, as well as programs capable of establishing and handling the communication with these tags. It is further to be understood that the smart devices may comprise near range communication technology such as RFID, NFC, Bluetooth, Ant, Zigbee, or the like.

The aim of the present disclosure is to remedy the drawbacks of the state of the art devices. This aim is solved by a medicament delivery device comprising the features of the independent patent claim. Preferable embodiments of the disclosure form the subject of the dependent patent claims.

According to an aspect of the disclosure, it comprises a medicament delivery device, provided with a housing, which housing is arranged to accommodate a medicament container filled with medicament. Further a drive unit comprising a plunger rod may be operable to act on the medicament container as well as a medicament delivery member guard movably arranged in said housing. A mechanical activation mechanism may be configured to interact with the drive unit and the medicament delivery member guard and wherein the mechanical activation mechanism may be movable between certain predetermined states when interacting with the drive unit.

Further, a recording unit capable of recording status changes of said medicament delivery device including the status of the mechanical activation mechanism may be included as well as detection elements operably connected to the recording unit and positioned such as to detect when the activation mechanism has been moved between certain predetermined states. With this configuration many different statuses may be detected and recorded by the recording unit, which statuses are coupled to occurrences such as priming and dose delivery of the medicament delivery device.

According to one aspect of the disclosure a plunger rod of the drive unit may in the release state be released to exert a pressure on the medicament inside the medicament container and wherein a medicament delivery member may be operably attached to the medicament container and arranged with manually operable activation elements, which activation elements, upon operation, are moved from a closed position to an open position of the interior of the medicament container for performing a priming operation of the medicament container.

According to one feasible solution, the mechanical activation mechanism may comprise a section of the plunger rod. The advantage with this solution is that the plunger rod is involved in many of the functions of a medicament delivery device having a number of automatic or semi-automatic functions.

Preferably the medicament delivery device further comprises a manually operated actuator that, when operated, alters the drive unit from a locked state to a release state. Thus, in the locked state, the medicament delivery device and all its functions are locked or inactive. It is only when the actuator is altered to the release state that the medicament delivery device is functional and can be used for delivering a dose of medicament.

Thus, when the actuator is operated such that the medicament delivery device is in the release state, the plunger rod of the drive unit is released and moved to exert a pressure on the medicament inside said medicament container, and the detection elements are arranged to detect the movement. The recording unit thus is informed that the medicament delivery device is active and ready for a priming operation. In order to perform a priming operation, a medicament delivery member assembly has to be attached.

Therefore, the medicament delivery device comprises a medicament delivery member assembly operably attached to the medicament container and arranged with manually operable activation elements, which activation elements, upon operation, are moved from a closed position to an open position of the interior of the medicament container for performing a priming operation of the medicament container.

In order to ascertain that the user is holding the medicament delivery device at the proper orientation when performing a priming operation, i.e. with the injection needle pointing generally vertically upwards, the recording unit may further comprise orientation elements capable of detecting angular positions of the medicament delivery device after activation, which orientation elements are activated by the detection elements detecting movement of the plunger rod. The recording unit may further comprise information elements capable of providing a user with information regarding correct angular positions of the medicament delivery device for a priming operation. In addition or instead, the information elements may be capable of providing a user with information regarding erroneous angular positions of the medicament delivery device for a priming operation.

In order to inform the user of the handling of the medicament delivery device, the information elements may comprise any or combinations of light emitting elements, sound emitting elements, vibration emitting elements, visual display elements.

Further, when the plunger rod is moved during priming, its movement may detected by the detection elements, whereby the recording unit switches off said orientation elements. This is because the orientation elements have performed their function as the medicament delivery device is primed with the proper orientation.

In addition, the medicament delivery device may further comprise a medicament delivery member guard movably arranged in the housing between a retracted position and an extended position covering the medicament delivery member after the priming operation. The medicament delivery member is thus hidden from view for the subsequent penetration sequence. Thus, the medicament delivery member guard is movable from the extended position to the retracted position during a penetration operation at a dose delivery site.

Further, the medicament delivery member guard may preferably be operably connected to the drive unit wherein the medicament delivery member guard releases the plunger rod in the retracted position, causing a dose of medicament to be delivered through the medicament delivery member, wherein the detection elements are arranged to detect when the plunger rod has been released. Again, the functions and movements of the plunger rod are used for detecting different operational statuses of the medicament delivery device.

One feature is that the detection of the movement of the plunger rod by the detection elements comprises a timer of the recording unit that is activated when the plunger rod has been released. The timer may then be used such that the recording unit activates the information elements when the timer has counted a pre-set time period to indicate that the medicament delivery device can be removed from the dose delivery site.

Preferably the recording unit may further comprise a micro control unit programmed to handle data obtained from the detection elements and to provide information via the information elements. In addition, the recording unit may further comprise data storage elements.

In addition, the recording unit may further comprise wireless communication elements for wireless transfer of data to and from the recording unit. In this regard, the communication elements comprise near range technology or as an alternative cellular radio communication technology.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which FIG. 1 is an exploded view of a medicament delivery device comprising a recording unit;

FIG. 2A is a cross-sectional view of the medicament delivery device of FIG. 1;

FIG. 2B is a cross-sectional view of the medicament delivery device of FIG. 1;

FIG. 4 is a detailed view of components and elements comprised in the medicament delivery device of FIG. 1;

FIG. 5 is a detailed view of components and elements comprised in the medicament delivery device of FIG. 1;

FIG. 10 is a detailed view of components and elements comprised in the medicament delivery device of FIG. 1;

FIG. 11 is a detailed view of components and elements comprised in the medicament delivery device of FIG. 1;

FIG. 12 is a detailed view of components and elements comprised in the medicament delivery device of FIG. 1;

FIG. 13 is a detailed view of components and elements comprised in the medicament delivery device of FIG. 1;

DETAILED DESCRIPTION

Figure 3:
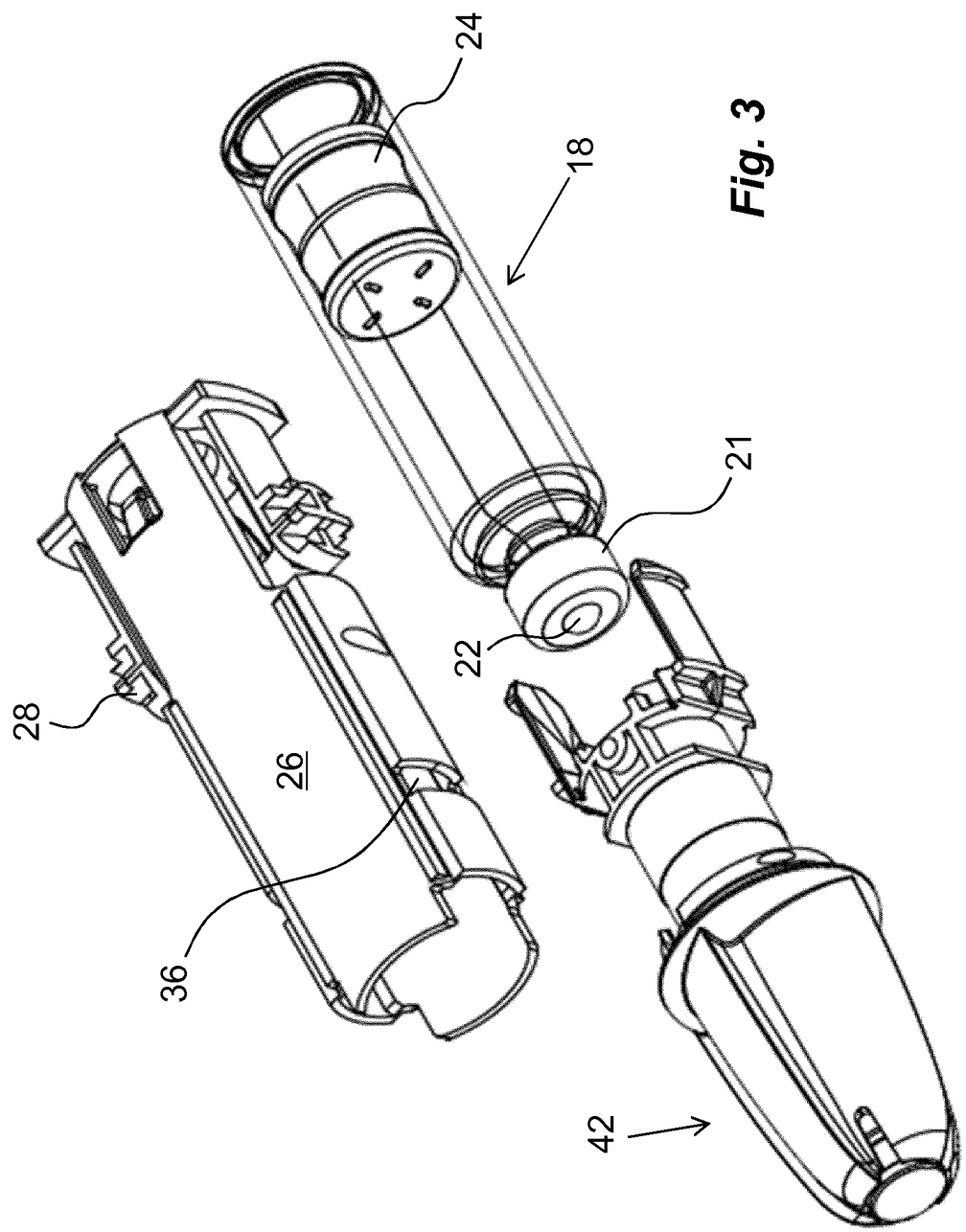
FIG. 3 is a detailed view of components and elements comprised in the medicament delivery device of FIG. 1.

The embodiment shown in the drawings comprises an elongated housing 10 having a proximal end 12 and a distal end 14, FIGS. 1 and 4. Windows 16 are arranged on the housing 10 for viewing a medicament container 18. An annular ledge 19 on the inner surface of the housing is positioned in the distal area as seen in FIG. 4. Stop ledges 20 are further arranged on the inner surface of the housing adjacent and distal of the annular ledge 19. The medicament container 18 has a generally tubular body with a proximal neck portion 21, FIG. 3. The proximal end of the neck portion is closed by a penetrable septum 22. In a distal area of the body a stopper 24 is placed. The medicament container 18 is designed to be placed in a medicament container holder 26 that preferably is made of a transparent material, FIG. 5. The medicament container holder 26 is provided with arms 27 that extend in the longitudinal direction, being flexible in the radial direction. The free ends of the arms are provided with outwardly extending protrusions 28, which protrusions 28 fit into recesses 30 in the wall of the housing 10 for fixating the medicament container holder 26 with the housing 10. The medicament container 18 is intended to be inserted into the medicament container holder 26 from a proximal end. To this end the distal end of the medicament container holder 26 is provided with a circumferential end wall 32 to provide a stop surface. Further, the distal area of the medicament container holder 26 is provided with distally directed, inwardly inclined arms 34 arranged to be in contact with the outer wall of the medicament container 18 to prevent rattling. At the proximal end of the medicament container holder 26, generally rectangular cut-outs 36 are provided. The distal end wall is further arranged with a central circular passage 38. The circular passage 38 is provided with radially inwardly directed protrusions 40 positioned on opposite sides.

Figure 6:
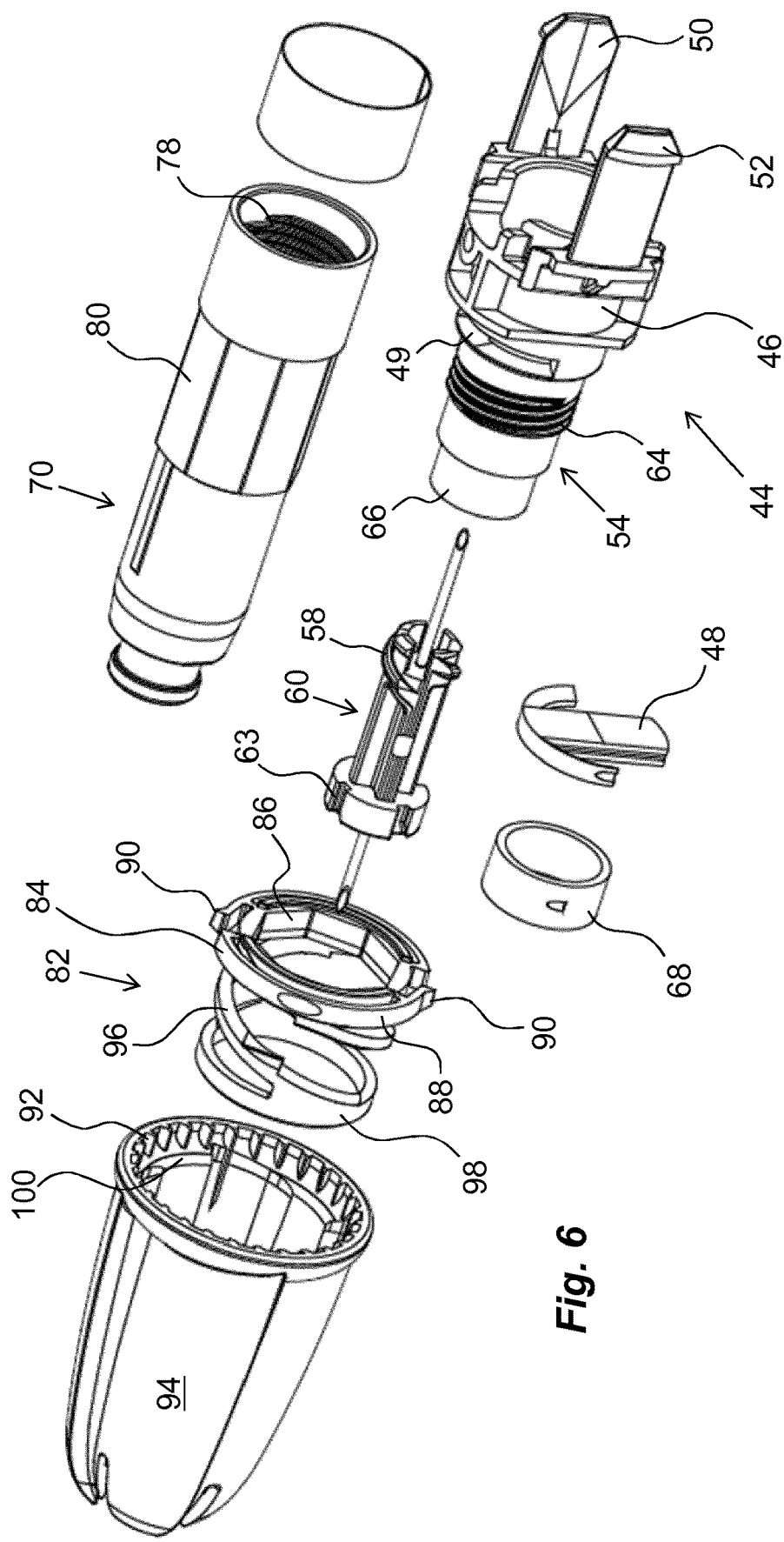
FIG. 6 is a detailed view of components and elements comprised in the medicament delivery device of FIG. 1.
Figure 7:
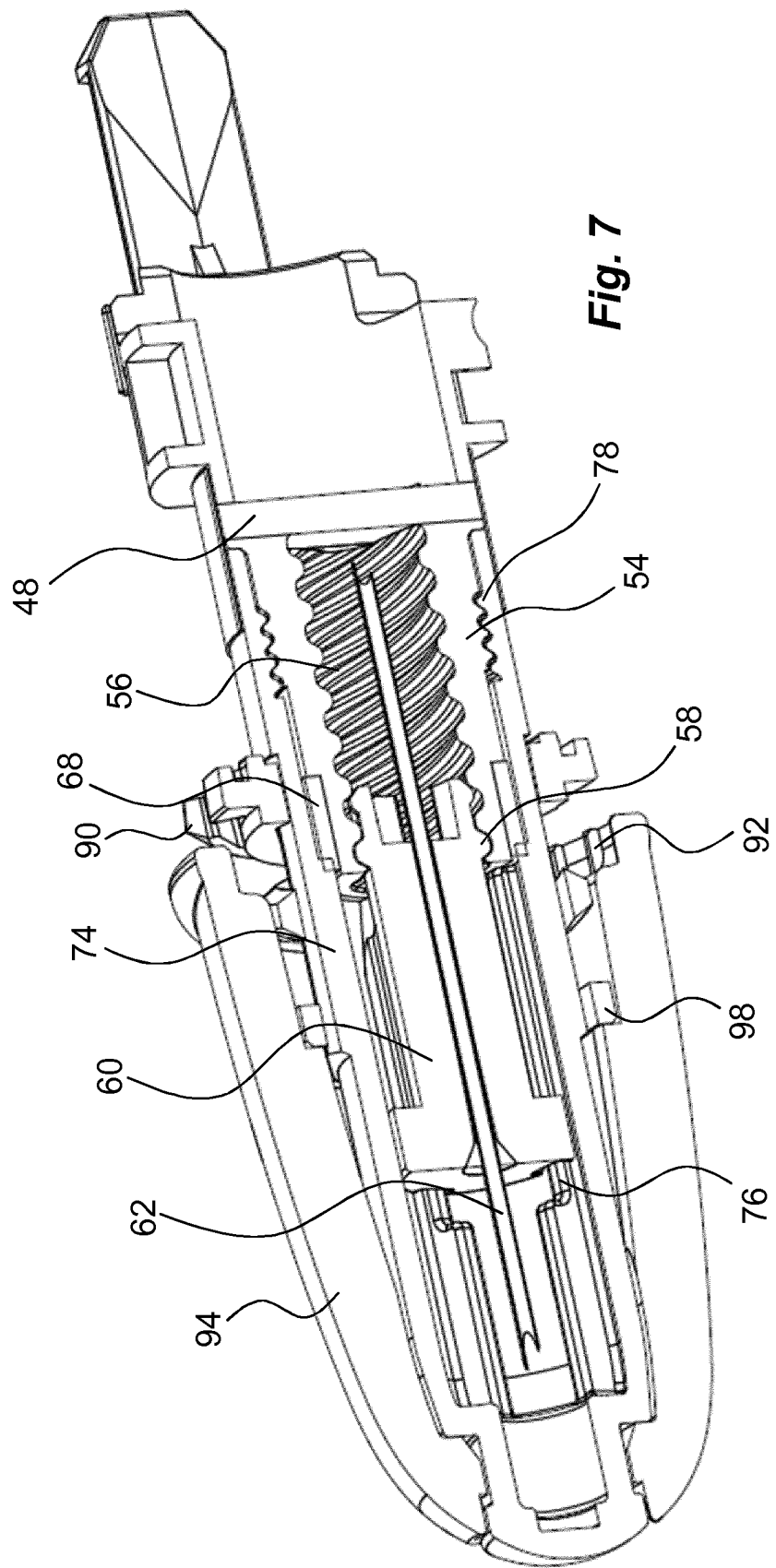
FIG. 7 is a detailed view of components and elements comprised in the medicament delivery device of FIG. 1.

Further a medicament delivery member assembly 42 is provided, FIGS. 1, 6 and 7. It comprises an attachment element 44 having a generally tubular body 46. The inner space of the body 46 is arranged to accommodate the neck portion 21 of the medicament container 18. Proximally of, and adjacent, the neck portion of the medicament container a transversal wall 48 is provided. The wall 48 may be an integral part of the attachment element but may also be a separate part as seen in FIG. 6 in the form of a plate that is pushed into a slit 49 having a transversal extension. The body 46 is further arranged with distally extending arms 50, in the embodiment shown two oppositely positioned arms 50. The free ends of the arms 50 are arranged with outwardly directed ledges 52, which ledges 52 are designed to fit into the rectangular cut-outs 36 of the medicament container holder 26 when the arms 50 are pushed into the medicament container holder 26, whereby the attachment element 44 is connected to the medicament container holder 26. The attachment element 44 is further arranged with a proximal generally tubular part 54.

The inner surface of the proximal part 54 is provided with threads or thread segments 56. The threads 56 are arranged to cooperate with threads or thread segments 58 on an outer surface of an elongated needle hub 60. An injection needle 62 is attached to the needle hub 60, extending on both sides of the needle hub 60, wherein both ends of the injection needle 62 are pointed or staked. The needle hub 60 is arranged with an annular surface provided with a number of longitudinally extending grooves 63 positioned equidistantly along the circumference. The proximal part 54 of the body 46 is further arranged with threads 64 on an outer surface thereof and the proximal end of the proximal part 54 is arranged with a section 66 with lesser diameter. A generally tubular sealing element 68 of a resilient material is arranged to be fitted onto the section 66, the sealing element 68 having a diameter generally corresponding to the diameter of the rest of the proximal part.

The medicament delivery member assembly 42 is further arranged with an inner cap 70, provided with an elongated tubular body 74. The inner surface of the body 74 is arranged with longitudinally extending ribs 76, which ribs 76 are intended to fit into the grooves 63 of the needle hub 60, creating a rotational lock between the inner cap 70 and the needle hub 60, while allowing longitudinal movement between them. Further, the inner surface at the distal end of the inner cap is arranged with threads 78, which threads 78 are designed to cooperate with the threads 64 of the body of the attachment element 44. The outer surface of the inner cap 70 is provided with a number of planar surfaces 80 along its circumference creating a nut-shape as seen in a cross-sectional view. These surfaces 80 are arranged to cooperate with an outer cap clutch mechanism 82, FIG. 6, comprising a ring-shaped locking member 84, where the inner surface of the locking member 84 is arranged with planar surfaces 86, such that the locking member 84 fits together with the nut-shape of the inner cap 70 to form a rotational lock between the two components. The locking member 84 is further provided with first engagement members that in the embodiment shown comprise two radially flexible arms 88 that extend along the circumference of the locking member 84. The free ends of the arms 88 are arranged with outwardly directed protrusions 90.

The protrusions 90 of the locking member 84 are arranged to cooperate with second engagement members in the form of a ratchet 92 arranged on an inner surface of an outer cap 94 at its distal area. The ratchet 92 preferably has a shape that forms a wedge-shape as seen from the distal direction. The arms 88 with the protrusions 90 and the ratchet 92 are thus intended to cooperate such that the outer cap 94 can only bring the locking member 84 with it in one direction. In the opposite direction, the protrusions 90 of the arms 88 will slide over the ratchet 92 wherein the arms 88 will flex in the radial direction.

The cap clutch mechanism 82 further comprises clutch biasing means 96 arranged between the outer cap 94 and the locking member 84, said clutch biasing means 96 is capable of biasing the locking member 84 for keeping it in the disengaged position. The clutch biasing means 96 is a resilient member. In the embodiment shown in FIG. 6, the resilient member comprises a distal end that is fixedly connected to, or integrated with, the locking member 84 and a proximal end configured to abut against an abutting surface on the inner surface of the outer cap 94. The resilient member has a spiral shape and is integral with the locking member 84. The proximal end of the locking member 84 is preferably attached to, or integrated with, a contact member 98, in the embodiment shown as a ring. The contact member 98 is intended to be seated in a 100 ledge on the inner surface of the outer cap 94.

Figure 8:
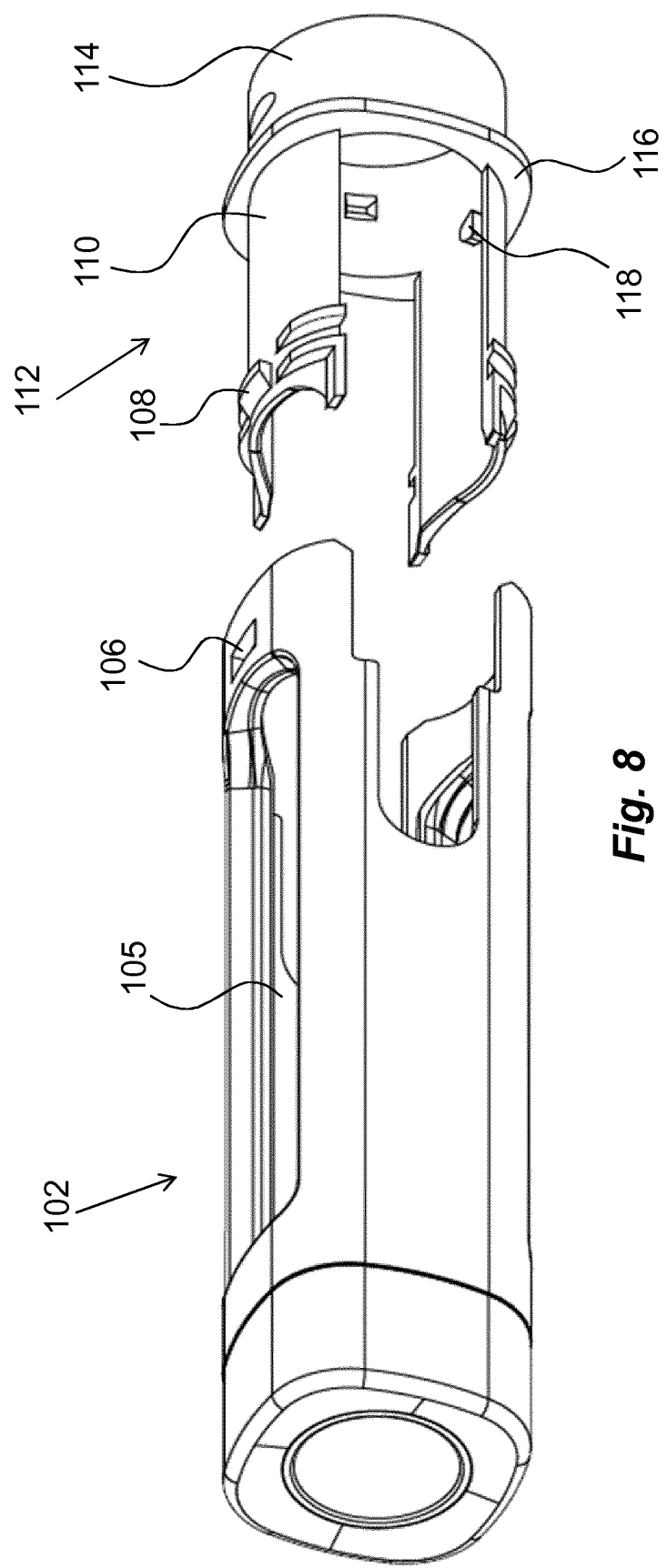
FIG. 8 is a detailed view of components and elements comprised in the medicament delivery device of FIG. 1.

The medicament delivery device is further arranged with a generally tubular medicament delivery member guard 102, FIGS. 1 and 8, arranged slidable inside the housing 10 and protruding through a proximal passage 104 thereof. The medicament delivery member guard 102 is further coaxial with and outside the medicament container holder 26. The side surface of the medicament delivery member guard 102 is arranged with rectangular cut-outs 105 providing possibility of viewing the medicament container 18 in the medicament container holder 26. The distal end area of the medicament delivery member guard 102 is provided with recesses or cut-outs 106 that are intended to cooperate with radially outwardly extending ledges 108 on proximally directed arms 110 of a medicament delivery member guard extension 112. The arms 110 of the medicament delivery member guard extension 112 are attached to a generally tubular body 114, FIG. 8. A radially outwardly extending annular ledge 116 is attached to the body 114, having a shape generally corresponding to the cross-sectional shape of the inner surface of the housing 10. The inner surface of the body 114 is arranged with inwardly directed protrusions 118. A medicament delivery member guard spring 119, FIGS. 1, 2A and 2B, is arranged between a distally directed surface of the annular ledge 116 of the medicament delivery member guard extension and a proximally directed surface of the annular ledge 19 of the housing 10 as seen in FIG. 2B.

Figure 9:
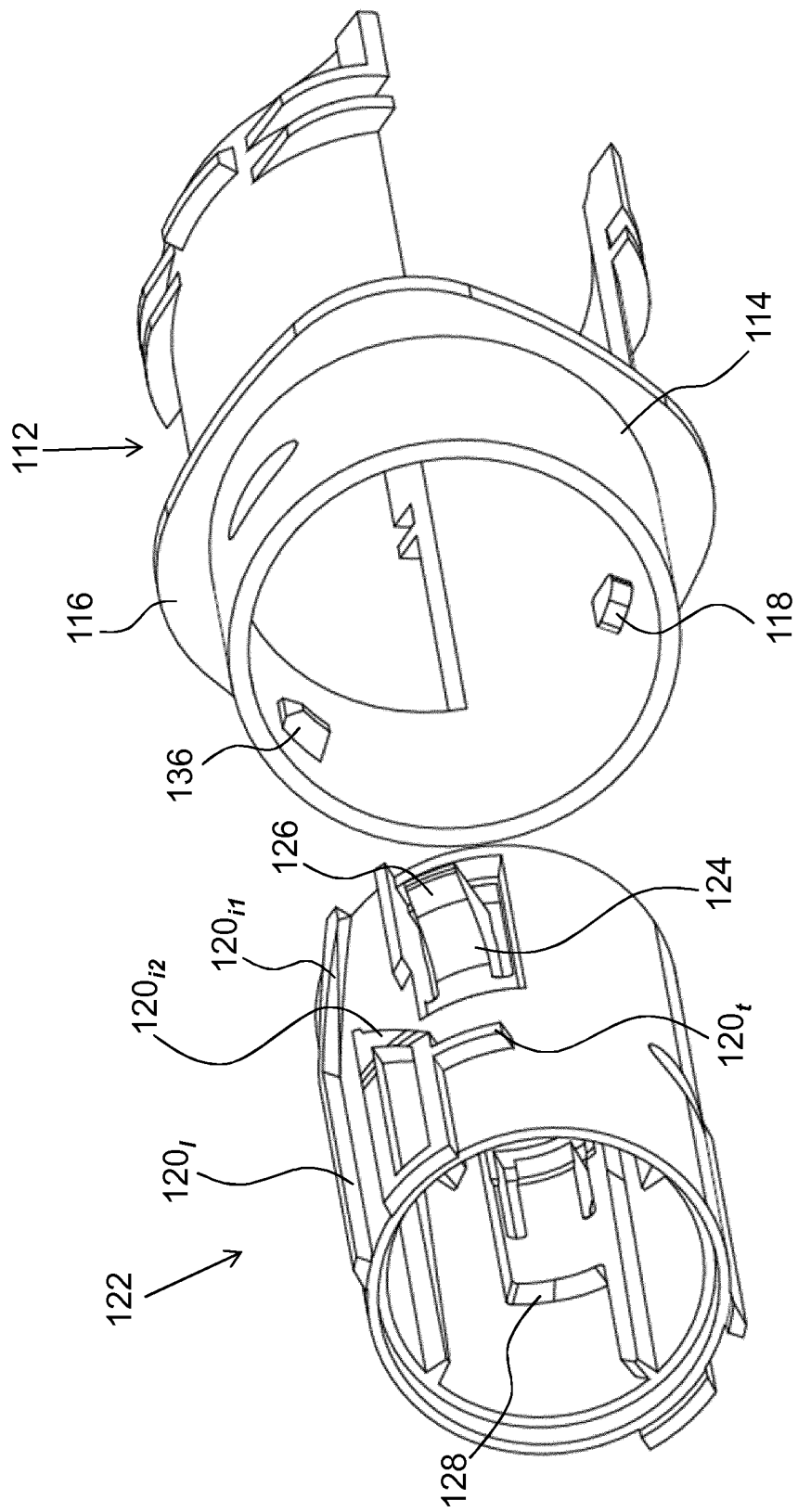
FIG. 9 is a detailed view of components and elements comprised in the medicament delivery device of FIG. 1.

The inwardly directed protrusions 118 are intended to cooperate with ledges 120 on an outer surface of a generally tubular rotator 122, FIGS. 1 and 9. The ledges 120 are divided into sections comprising a longitudinally extending section $120_l$, a first inclined section $120_{i1}$, a second inclined section $120_{i2}$ and a transversal section $120_r$. Further, in the vicinity of some ledges 120, proximally directed arms 124 are formed in the rotator wall, wherein the free ends of the arms 124 are arranged with wedge-shaped ledges 126. The inner surface of the rotator 122 is further arranged with transversal ledges 128. The rotator 122 is arranged to be rotatable as will be described, but is locked in the proximal, longitudinal direction by a distal surface of the medicament container holder 26.

In the distal direction, the rotator 122 is locked by a proximally directed surface of an actuator 130, FIG. 10, having a generally tubular body 132. The outer surface of the body 132 is arranged with radially outwardly directed ledges 134, which ledges 134 are to cooperate with second protrusions 136, FIG. 9, on the inner surface of the medicament delivery member guard extension 112 as will be described. The actuator 130 is further arranged with an annular ledge 138 forming a proximal surface. Proximal of the annular ledge 138 flexible tongues 140 are arranged in the body 132 extending in the distal direction. The free ends of the tongues 140 are arranged with outwardly extending ledges 142, the function of which will be explained below.

The proximal end of the actuator 130 is further arranged with a central passage 144. The central passage 144 is arranged with an inwardly directed ledge 146, which ledge is provided with two cut-outs 148 on opposite sides extending certain lengths along the circumference. The ledge 146 is designed to cooperate with stop ledges 150 on an outer surface of a plunger rod 152, FIG. 11, where the stop ledges 150 are positioned on opposite sides of the plunger rod 152. The plunger rod 152 is further arranged with longitudinally extending grooves 153, which grooves 153 are designed to cooperate with the inwardly directed protrusions 40 in the passage 38 of the medicament container holder 26, creating a rotational lock of the plunger rod 152 while allowing relative longitudinal movement. A drive spring 154, FIGS. 1 and 2, is further arranged inside the plunger rod 152 between a proximal end wall 156 of the plunger rod 152 and an end wall 158 of an actuator knob 160. A guide rod 162 is further provided inside the drive spring 154.

The actuator 130 is further arranged with distally directed arms 164, where the distal ends of the arms 164 are arranged with slits 166. The slits 166 are intended to accommodate proximally directed ledges 168 of the actuator knob 160, which ledges 168 are attached to a distal end wall of the actuator knob 160, FIG. 10. The slits 166 and the ledges 168 form a rotational lock between the components. The actuator knob 160 is further arranged with a tubular body 170 having an outer diameter that generally corresponds to the distal inner diameter of the actuator 130. The body 170 of the actuator knob 160 is further arranged with generally radially flexible arms 172 that extend in the distal direction. The free ends of the arms 172 are arranged with outwardly directed ledges 174, which ledges 174 are designed to fit into recesses 176 of the actuator 130. The interaction between the arms 172 and the recesses 176 causes a locking in the longitudinal direction between the components. A longitudinally extending ledge 177 is positioned adjacent the recess 176, which ledge 177 will function as a rotation limiter for the actuator knob in cooperation with the stop ledges 20 of the housing.

The actuator knob 160 is further provided with a mark, arrow or other indicia 178 on its outer surface, FIG. 12. The mark 178 is intended to be used together with two indicia 180 on an outer surface of the distal end of the housing 10. These indicia 180 could for example be a symbol of a padlock, where one, 180*a*, is locked and one, 180*b*, is open.

The distal end of the plunger rod 152 is further arranged with a section 182, FIG. 11, comprised in an activation mechanism, that extends into the interior of the actuator knob 160. The section 182, which may be seen as an extension of the plunger rod 152 in the distal direction, is formed as half of the tubular plunger rod wherein the remaining half is arranged with a rectangular cut-out 184 adjacent the full plunger rod 152 and a rectangular passage 186 placed distally of the cut-out. The cut-out 184 and the passage 186 are also parts of the activation mechanism as will be described.

The actuator knob 160 is further arranged to accommodate a recording unit 190, FIGS. 10 and 13. The recording unit 190 is preferably arranged inside a housing 192, attached to the actuator knob 160. The recording unit preferably comprises an electronic circuit 194 arranged on a printed circuit board 196. The electronic circuit 194 comprises a micro control unit or processor 198, capable of processing data program code for performing different tasks. The data program code is preferably stored in appropriate memory elements 200, in which also retrieved data may be stored, as will be described. The electronic circuit 194 is further arranged with some power supply 202 such as button cells, photovoltaic panels, etc. When a button cell is used, a holder 203 is then provided, designed to provide electrical connection between the button cell 202 and the printed circuit board 196. Further, an activator element 204 is electronically connected to the electronic circuit 194. In the embodiment shown the activator element is in the form of a switch that is mechanically activated. It is however to be understood that many other types of activator elements may be used for obtaining the functions that will be descried. Also a gravitational sensor 206 is provided in the electronics circuit functioning as an orientation element as will be described.

The electronic circuit 194 may further be arranged with a user communication circuit 208 that is arranged and programmed to communicate with a user. The user communication circuit 208 may comprise display elements that can communicate visually, e.g. by text stored in the electronics module that is displayed on a suitable display 210 on the housing of the recording unit 190. Instead of text or the like indicia, lights with different colours may be used to provide information to the user. In addition to, or instead, the user communication circuit may comprise audio elements 212 that can communicate audibly, e.g. by certain sounds that correspond to certain status conditions or a recorded message stored in the electronics module that is played in an appropriate loudspeaker of the electronics module or of the device as such.

A further development of the activation function is to provide the recording unit 190 with at least one communication circuit 214. The communication technologies that the communication circuit 214 may utilize may comprise near range communication technology such as RFID, NFC or the like, as well as Bluetooth, Ant, ZigBee, just to mention a few. This type of wireless communication technology may also be used to activate the recording unit. The communication circuit may be used for monitoring the usage of the medicament delivery device such that information is transmitted from the medicament delivery device to the recording unit.

According to a possible feature, if the recording unit 190 is provided with communication circuits, then monitored data obtained by the recording unit may be transferred to external storage sources and/or external devices. If for instance NFC technology is used, then a mobile NFC-enabled device may derive the monitored data from the usage management module. The same functionality may also be provided when using Bluetooth communication technologies.

The mobile device may then either be capable of processing the data, such as e.g. calculating the time and date of an occurrence of the medicament delivery device, or may in turn transmit the monitored data to external databases via the communication technologies of the mobile device, such as cellular radio communication networks, e.g. GSM, 3G, 4G, etc. and/or wireless local area networks, which networks can provide access to the internet and thus to a large number of external data storage sources, data handling centres, etc.

Regarding communication technologies, it is of course possible to incorporate the above mentioned communication technologies in the recording unit 190 as such. Then the recording unit may communicate directly with external data storage sources, data handling centres etc. via the communication networks. The monitored data may preferably be accessible to a physician or the like skilled person that is responsible for the treatment of the user of the medicament delivery device and who might have put together a treatment scheme. This retrieved monitored data may then be evaluated to derive information such as adherence, and the lack of which may lead to measures from the physician.

Figure 14:
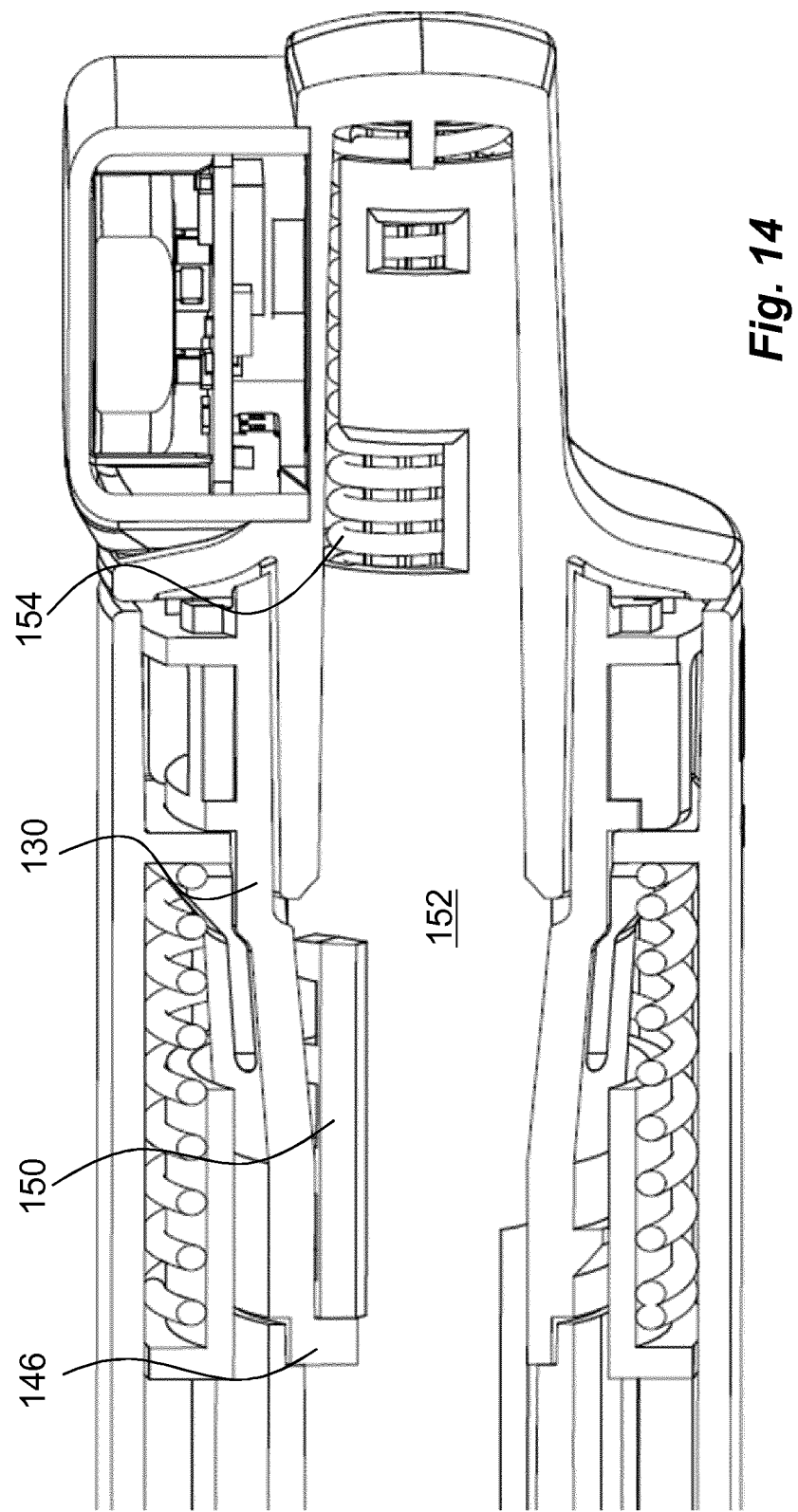
FIG. 14 is a functional view of the medicament delivery device of FIG. 1 during a different functional stage.
Figure 15:
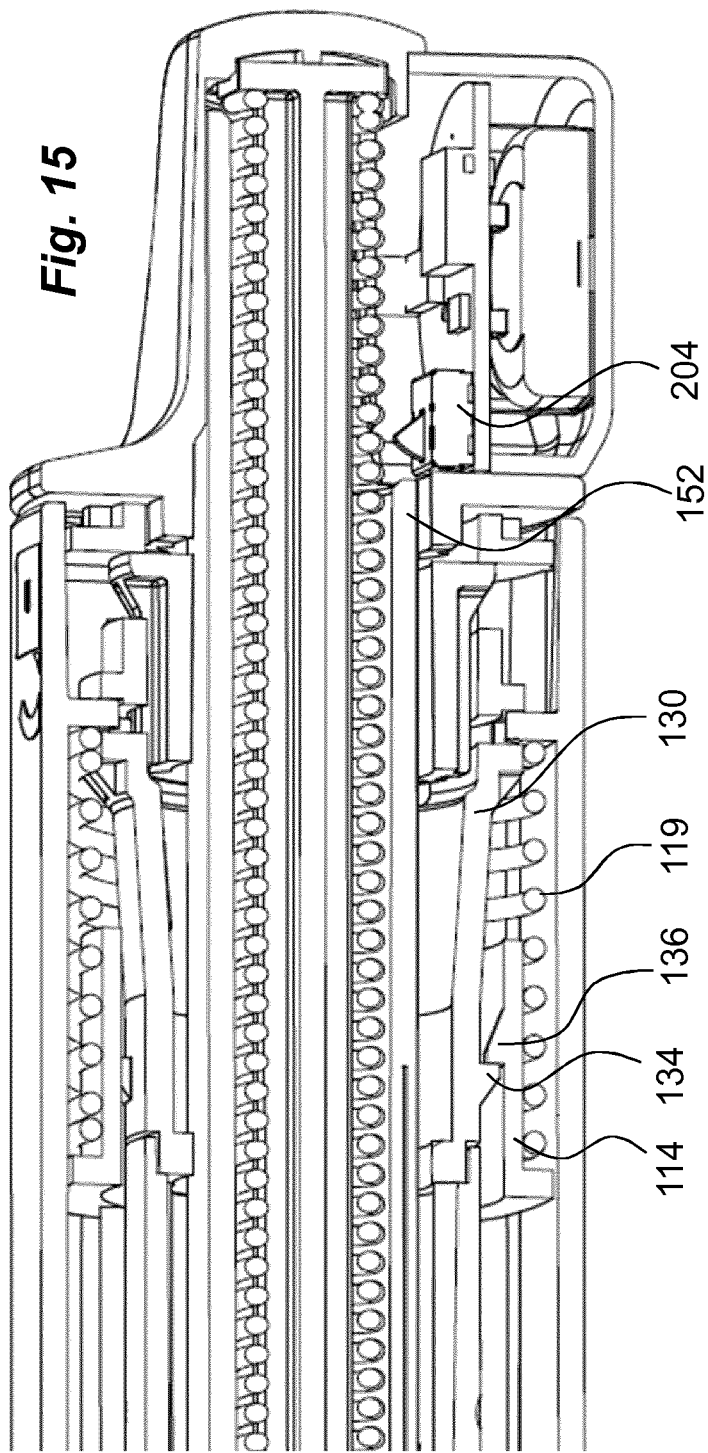
FIG. 15 is a functional view of the medicament delivery device of FIG. 1 during a different functional stage.
Figure 16:
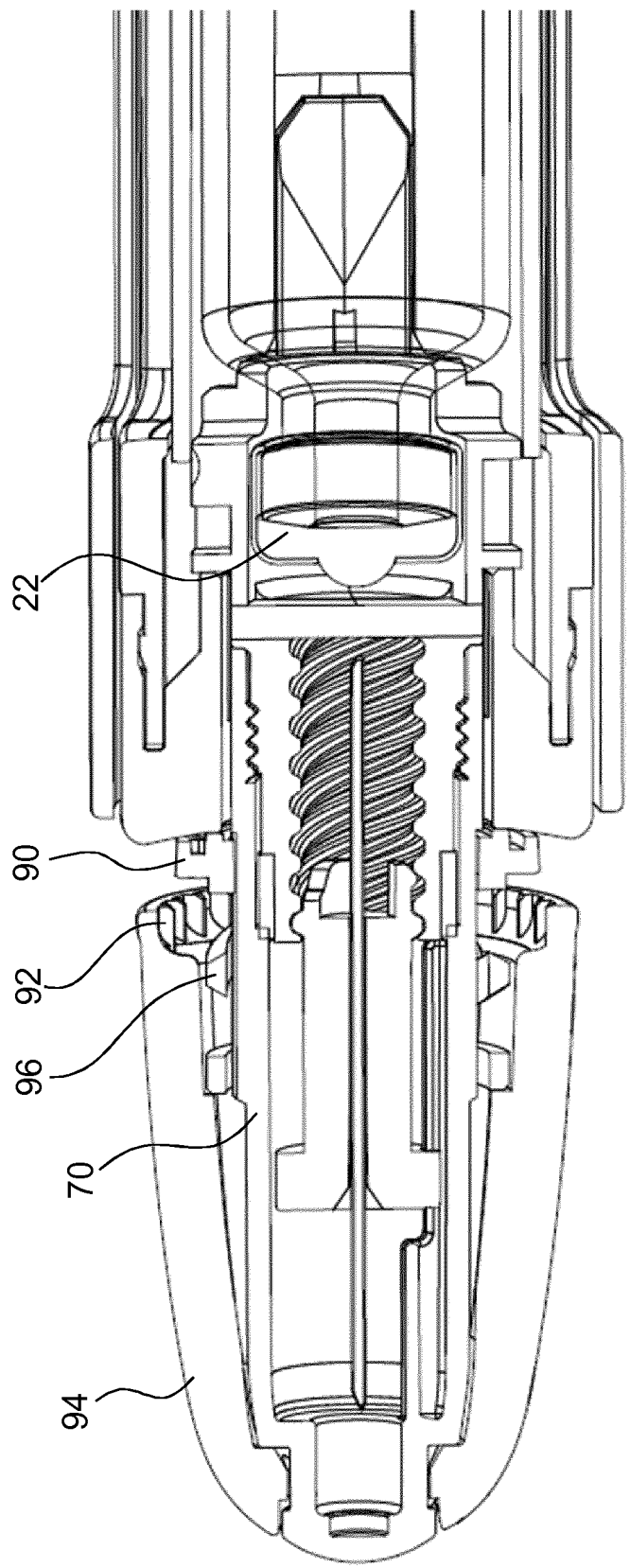
FIG. 16 is a functional view of the medicament delivery device of FIG. 1 during a different functional stage.

The device is intended to function as follows. When the medicament delivery device is delivered to a user, it is provided with a medicament container 18 in the medicament container holder 26. The plunger rod 152 is positioned in its most distal position with the drive spring 154 tensioned. The plunger rod 152 is held in this position by the proximal end surfaces of the ledges 150 on its outer surface resting on the inwardly directed ledges 146 of the actuator 130, FIG. 14. Further the medicament delivery member guard 102 and its extension 112 is in its most distal position inside the housing 10 and held there against the force of the medicament delivery member guard spring 119 by the protrusions 136 of the medicament delivery member guard extension 112 resting on the ledges 134 on the outer surface of the actuator 130. The actuator knob 160 is in a position where its indicator is pointing on the lock symbol 180a on the housing. Thus the medicament delivery device is locked. Further, the recording unit is switched off since the activation switch is not affected as seen in FIG. 15. Also, the outer cap 94 of the medicament delivery member assembly is rotating freely around the inner cap 70, and the cap clutch mechanism 82 is out of engagement with the ratchet 92 of the outer cap 94 by the biasing means 96, as shown in FIG. 16, whereby it is not possible to remove the medicament delivery member assembly.

When the medicament delivery device is to be used, it is unlocked in that the actuator knob 160 is turned about ninety degrees, indicted by the mark 178 being moved to the unlocked indicia 180b. Since the actuator knob 160 is rotatably locked to the actuator 130, the latter will also rotate. The turning of the actuation knob 160 and the actuator 130 is limited by the ledges 177 on the actuator coming in contact with the stop ledges 20 of the housing. The rotation of the actuator 130 will cause several actions. The plunger rod 152 is rotatably locked in relation to the medicament container holder 26 by the grooves on the plunger rod 152 cooperating with the protrusions 40 on the passage 38 of the medicament container holder 26. The medicament container holder 26 is in turn rotatably locked in the housing as mentioned above. Thus, the rotation of the actuator 130 will cause the ledges 146 of the central passage 144 of the actuator 130 to move out of contact with the stop ledges 150 of the plunger rod 152, whereby the plunger rod 152 is free to move in the proximal direction due to the force of the drive spring 154. The plunger rod 152 then pushes the stopper 24 in the proximal direction, causing a pressure in the medicament container 16. However, since the medicament container is closed in that the distal end of the needle 62 has not yet penetrated the septum 22 of the medicament container 16, the movement is stopped.

Figure 17:
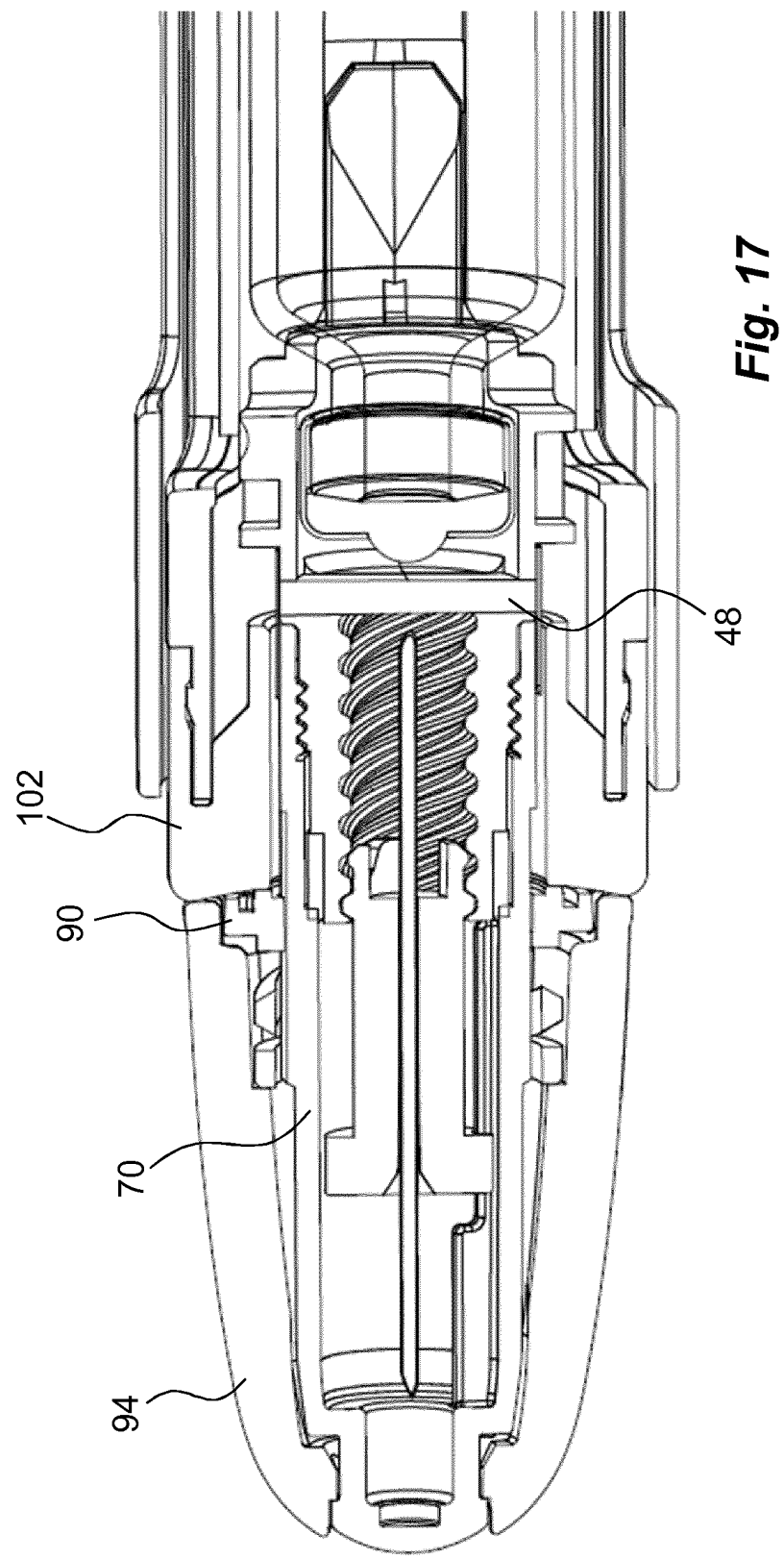
FIG. 17 is a functional view of the medicament delivery device of FIG. 1 during a different functional stage.
Figure 18:
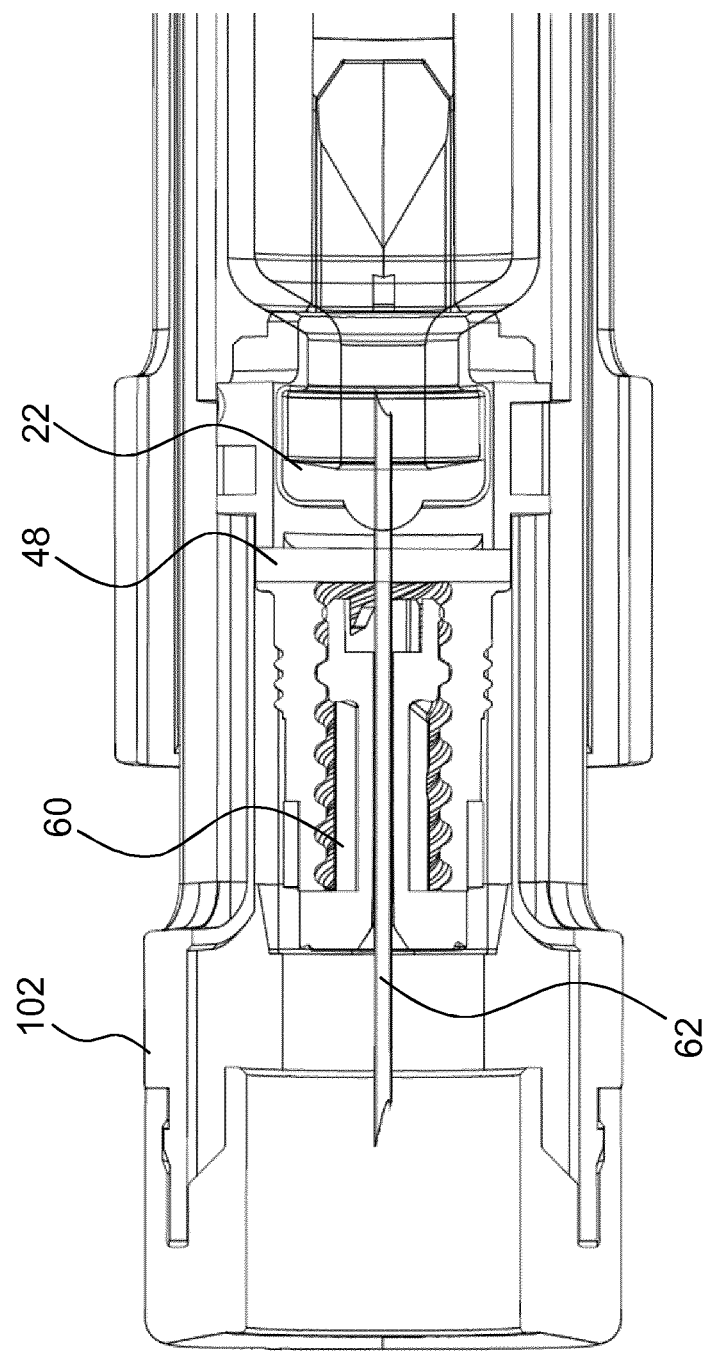
FIG. 18 is a functional view of the medicament delivery device of FIG. 1 during a different functional stage.

Further, the medicament delivery member guard 102 is rotatably locked in relation to the housing 10 and the rotation of the actuator 130 will further cause the outwardly directed ledges 134 of the actuator 130 to move out of contact with the second protrusions 136 on the inner surface of the medicament delivery member guard extension 112. Thus, the medicament delivery member guard 102 is now free to move in the proximal direction by the medicament delivery member guard spring 119. The movement of the medicament delivery member guard 102 will cause its proximal end to come in contact with the cap clutch mechanism 82 such that it is moved to connect the outer cap 94 with the inner cap 70, FIG. 17. With the engagement of the outer cap 94 with the inner cap 70, turning of the outer cap 94 to remove it proximally causes the inner cap 70 to also rotate, whereby the hub 60 is screwed distally into the attachment element 44 whereby the pointed distal end of the needle 62 penetrates the transversal wall 48 and subsequently the septum 22 of the medicament container, FIG. 18. Finally, the outer cap 94 and the inner cap 70 can be removed. When the medicament delivery member assembly has been removed the medicament delivery member guard 102 is moved to its extended position by the medicament delivery member guard spring 119, covering the needle 62. The movement of the medicament delivery member guard 102 and the medicament delivery member guard extension 112 will cause the inwardly directed protrusions 118 on the medicament delivery member guard extension to come in contact with the first inclined sections $120_{i1}$ of the rotator 122, whereby the rotator 122 is turned a certain angle.

Figure 19:
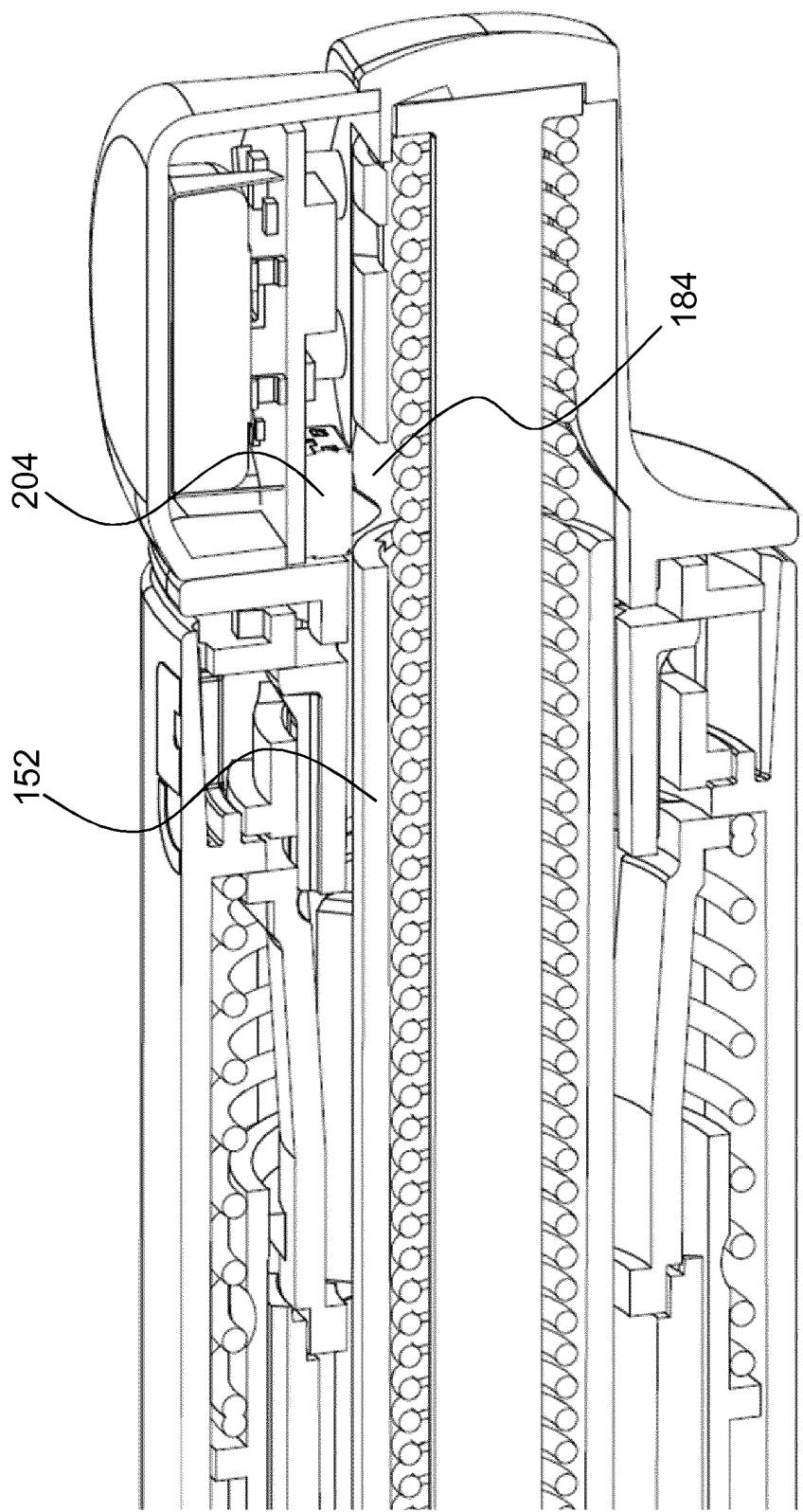
FIG. 19 is a functional view of the medicament delivery device of FIG. 1 during a different functional stage.
Figure 20:
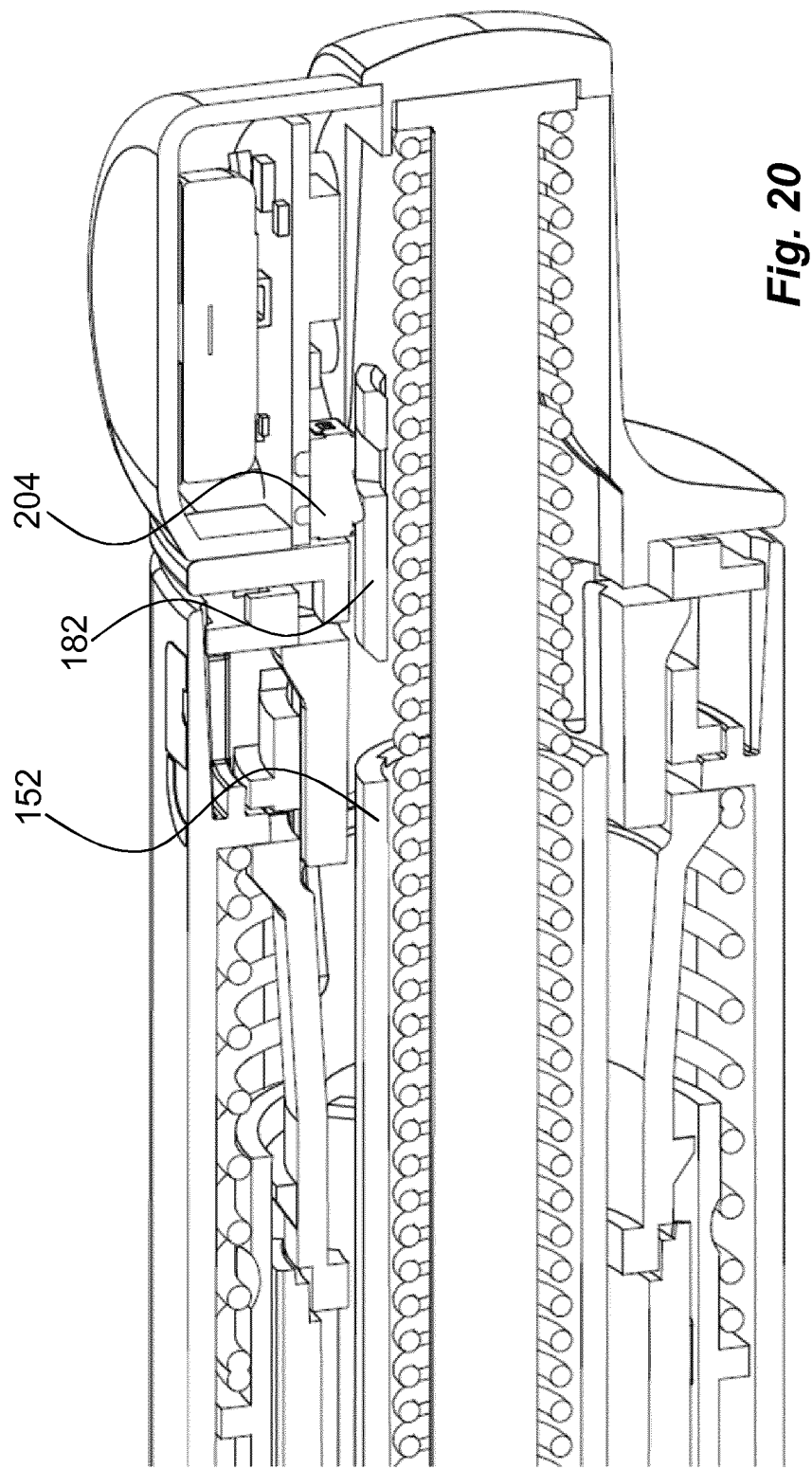
FIG. 20 is a functional view of the medicament delivery device of FIG. 1 during a different functional stage.

The turning of the actuator knob 160 will further cause the electronics of the actuator knob to be turned whereby the activator element 204 will enter the cut-out 184 of the plunger rod 152, FIG. 19, but when the plunger rod 152 is released as mentioned above and moved proximally, the activator element 204 will come in contact with a surface of the section 182 of the plunger rod 152 distally of the cut-out 184, FIG. 20. This will activate the electronic circuit 194 to be operable. Since the electronics circuit 194 is provided with a gravitational sensor 206 it can detect how the medicament delivery device is oriented. When the medicament delivery member assembly 42 is operated to remove the caps 94, 70 and to have the needle 62 penetrating the septum 22 of the medicament container 18, the medicament delivery device should be held in a vertical direction with the needle 62 upwards in order to provide a correct priming function when the pressure inside the medicament container 18 is released through the needle 62.

Figure 21:
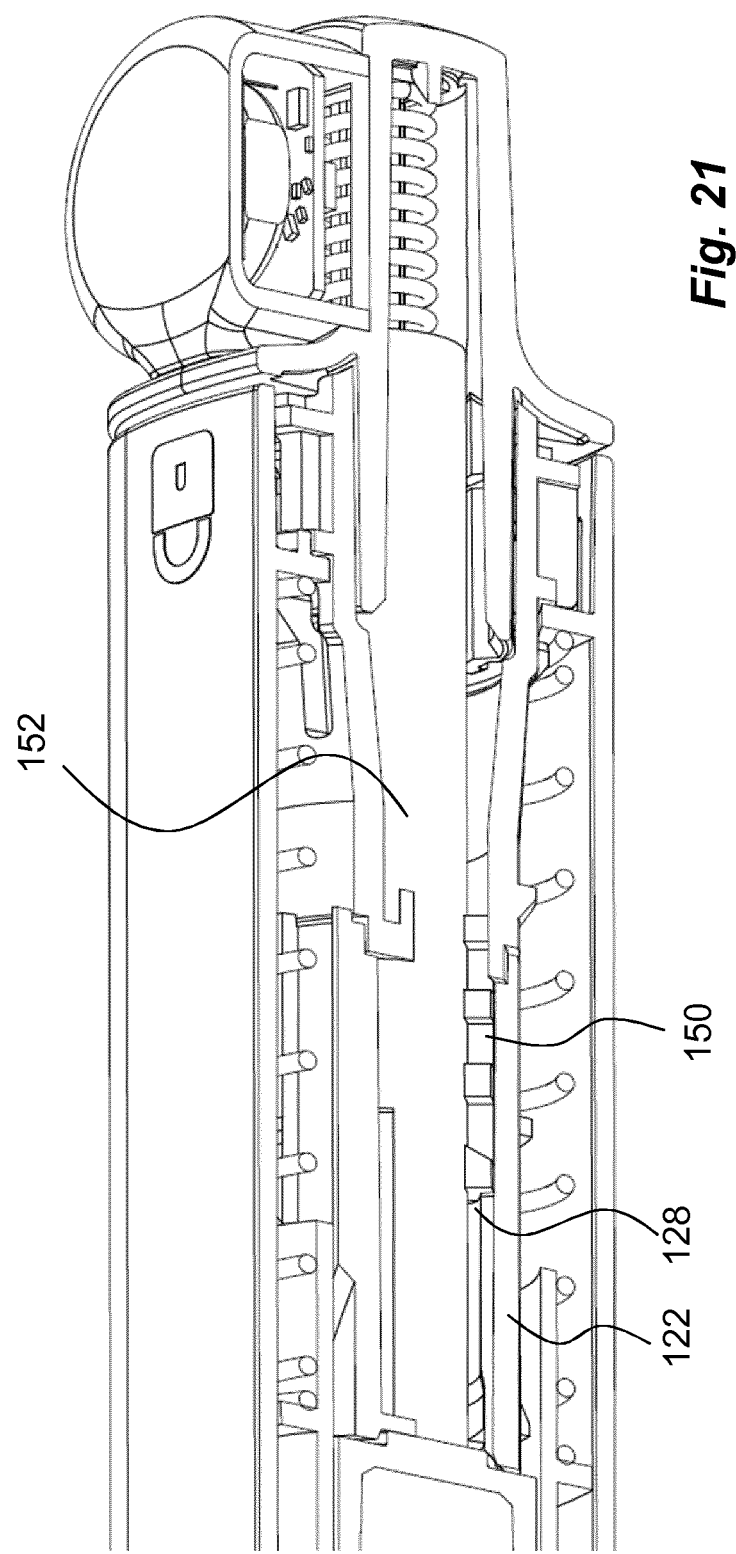
FIG. 21 is a functional view of the medicament delivery device of FIG. 1 during a different functional stage.
Figure 22:
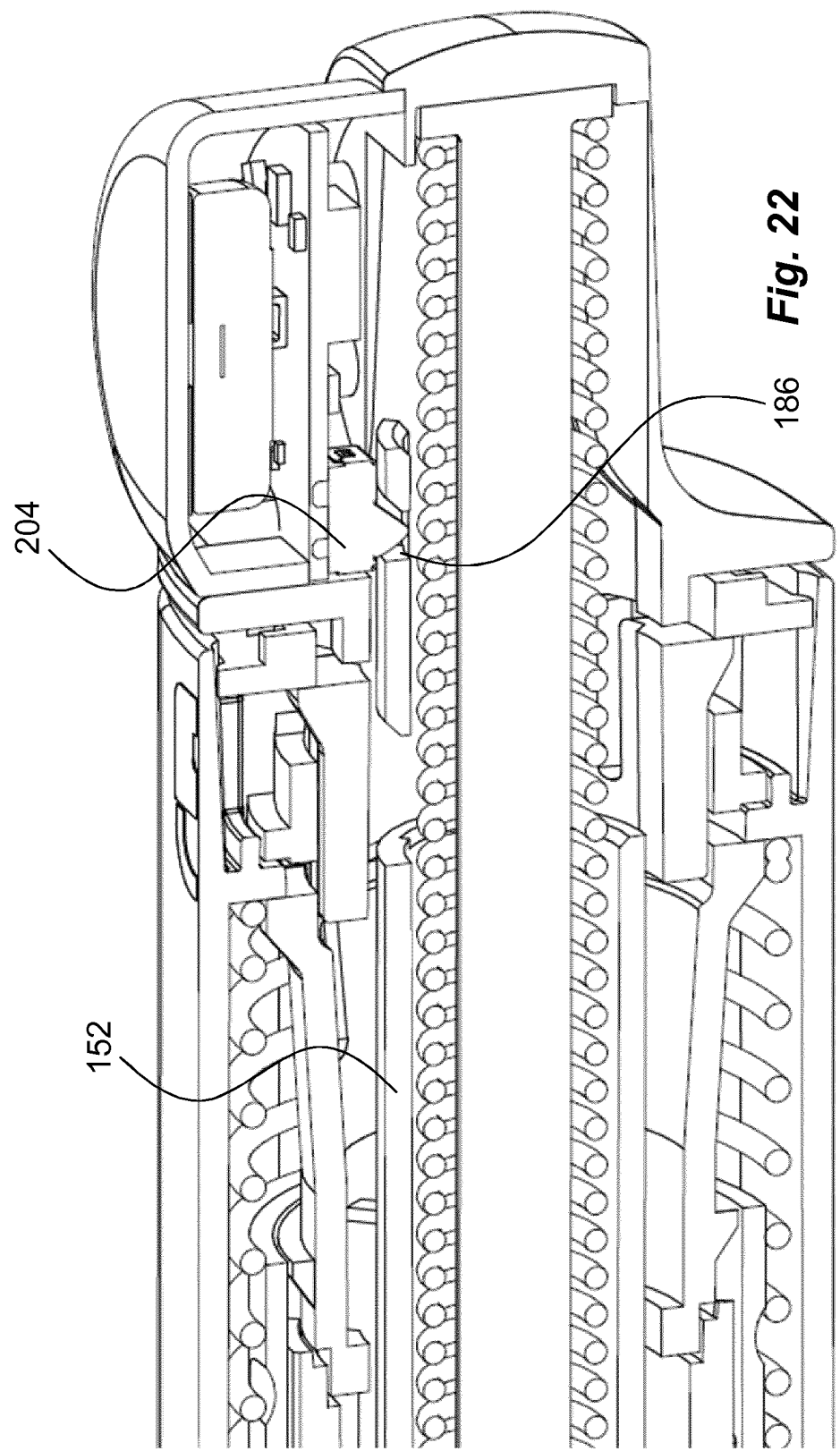
FIG. 22 is a functional view of the medicament delivery device of FIG. 1 during a different functional stage.
Figure 23:
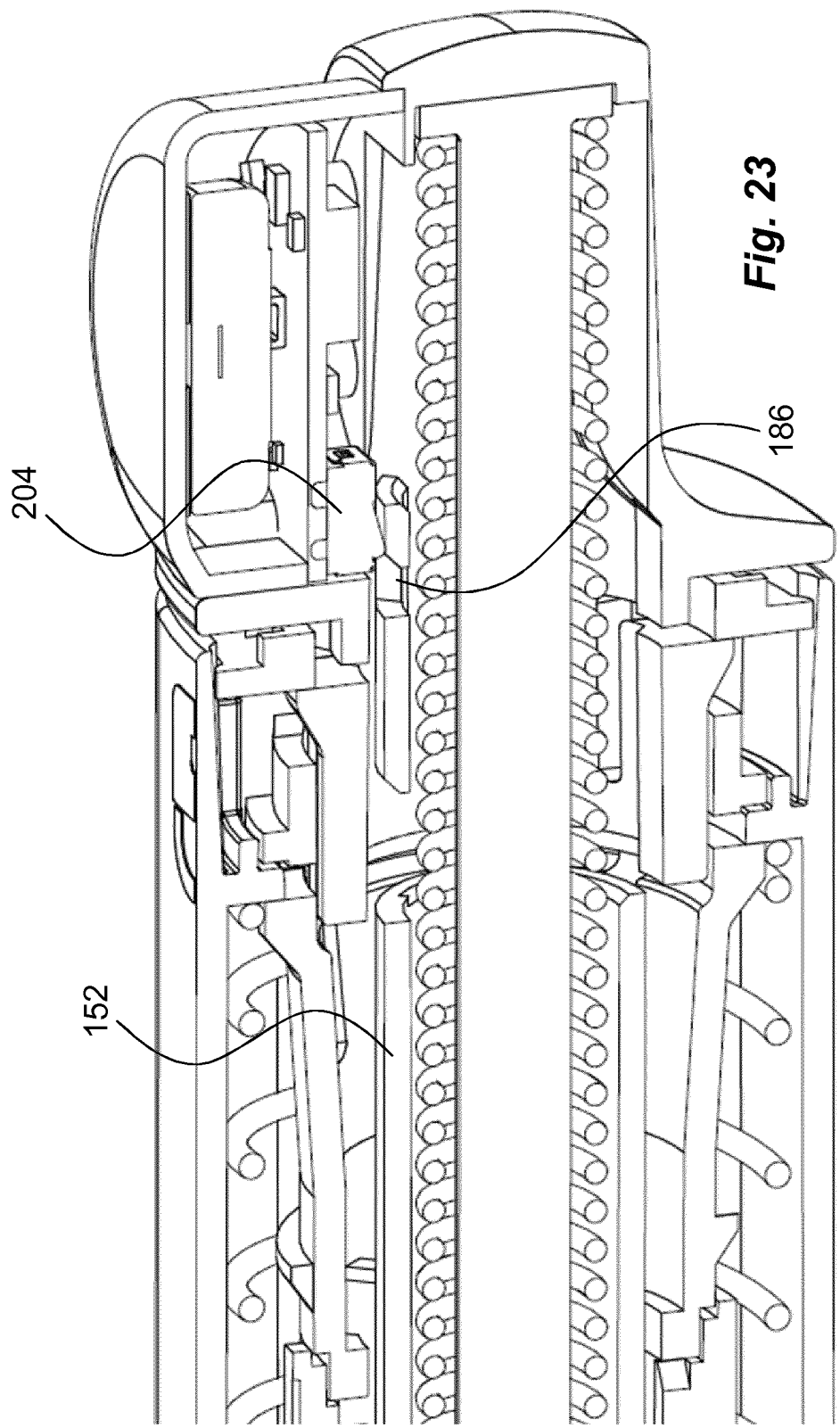
FIG. 23 is a functional view of the medicament delivery device of FIG. 1 during a different functional stage.

The gravitational sensor 206 may then provide information to the electronics circuit 194, whereby the electronics circuit 194 may provide information to the user whether the medicament delivery device is held correctly or not. This information may for example be provided by light with different colours visible on the display 210. For instance the colour may be green when the device is held correctly and may be red when the device is held incorrectly. During the priming sequence the plunger rod 152 is moved in the proximal direction until the proximally directed surfaces of the ledges 150 of the plunger rod 152 come in contact with the transversal ledges 128 on the inner surface of the rotator 122, FIG. 21, stopping the movement of the plunger rod 152. Further, when the plunger rod 152 moves proximally during priming, the activator element 204 will pass the rectangular passage 186 of the plunger rod, FIG. 22, thereby deactivating the switch when passing and then again activating when the activator element 204 has passed, FIG. 23. This causes the electronics circuit to switch off the gravitational sensor.

Figure 24:
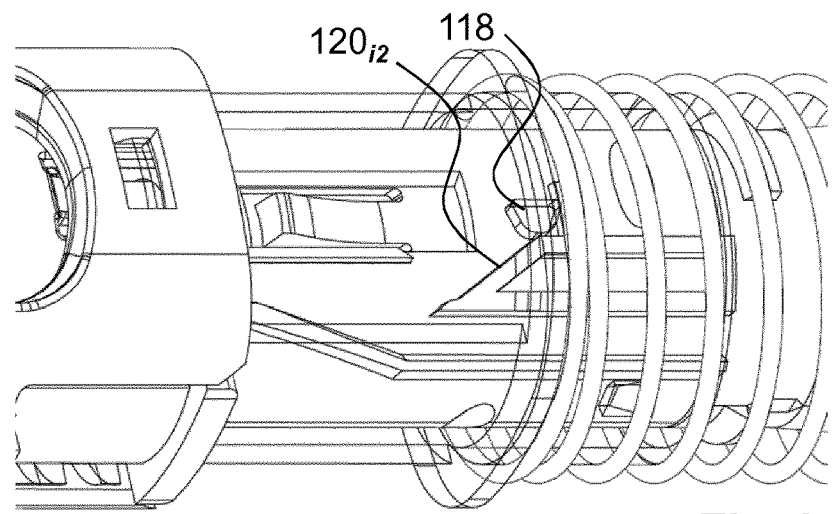
FIG. 24 is a functional view of the medicament delivery device of FIG. 1 during a different functional stage.
Figure 25:
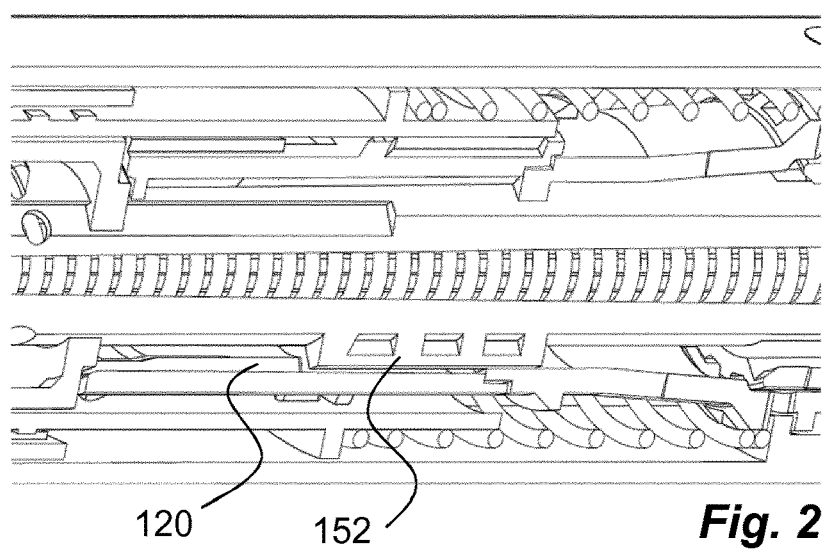
FIG. 25 is a functional view of the medicament delivery device of FIG. 1 during a different functional stage.
Figure 27:
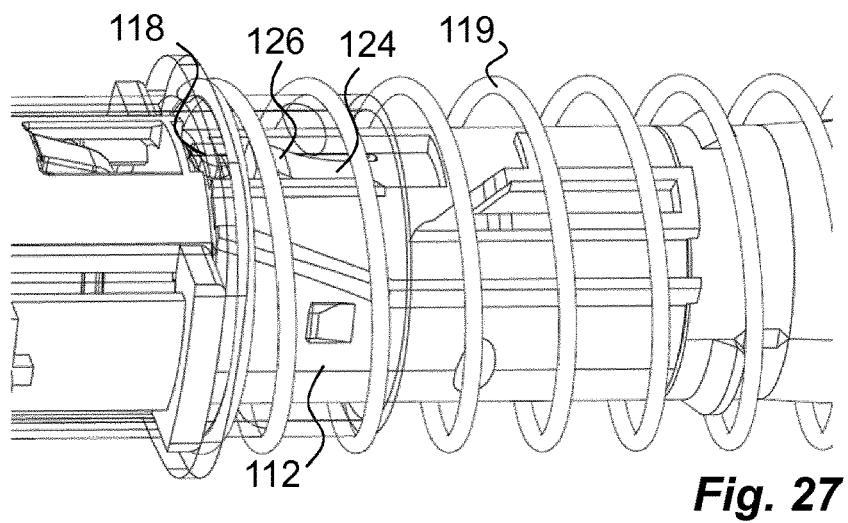
FIG. 27 is a functional view of the medicament delivery device of FIG. 1 during a different functional stage

The device is now ready for a dose delivery. The patient then presses the proximal end of the medicament delivery member guard 102 against a dose delivery site, whereby a penetration is performed when a medicament delivery member is an injection needle 62. The pressing against a dose delivery site also causes the medicament delivery member guard 102 and the medicament delivery member extension 112 to move distally in relation to the rest of the medicament delivery device, whereby the inwardly directed protrusions 118 of the medicament delivery member guard extension 112 will come in contact with the second inclined section $120_{i2}$ of the ledges 120 on the outer surface of the rotator 122, FIG. 24. This in turn causes the rotator 122 to rotate around the longitudinal axis, wherein the rotation will cause the ledges 150 of the plunger rod 152 to move out of contact with the transversal ledges 128 of the rotator 122, FIG. 25. The plunger rod 152 is again free to move in the proximal direction by the force of the drive spring 154, thereby moving the stopper so that a dose of medicament is delivered through the injection needle 62.

Figure 26:
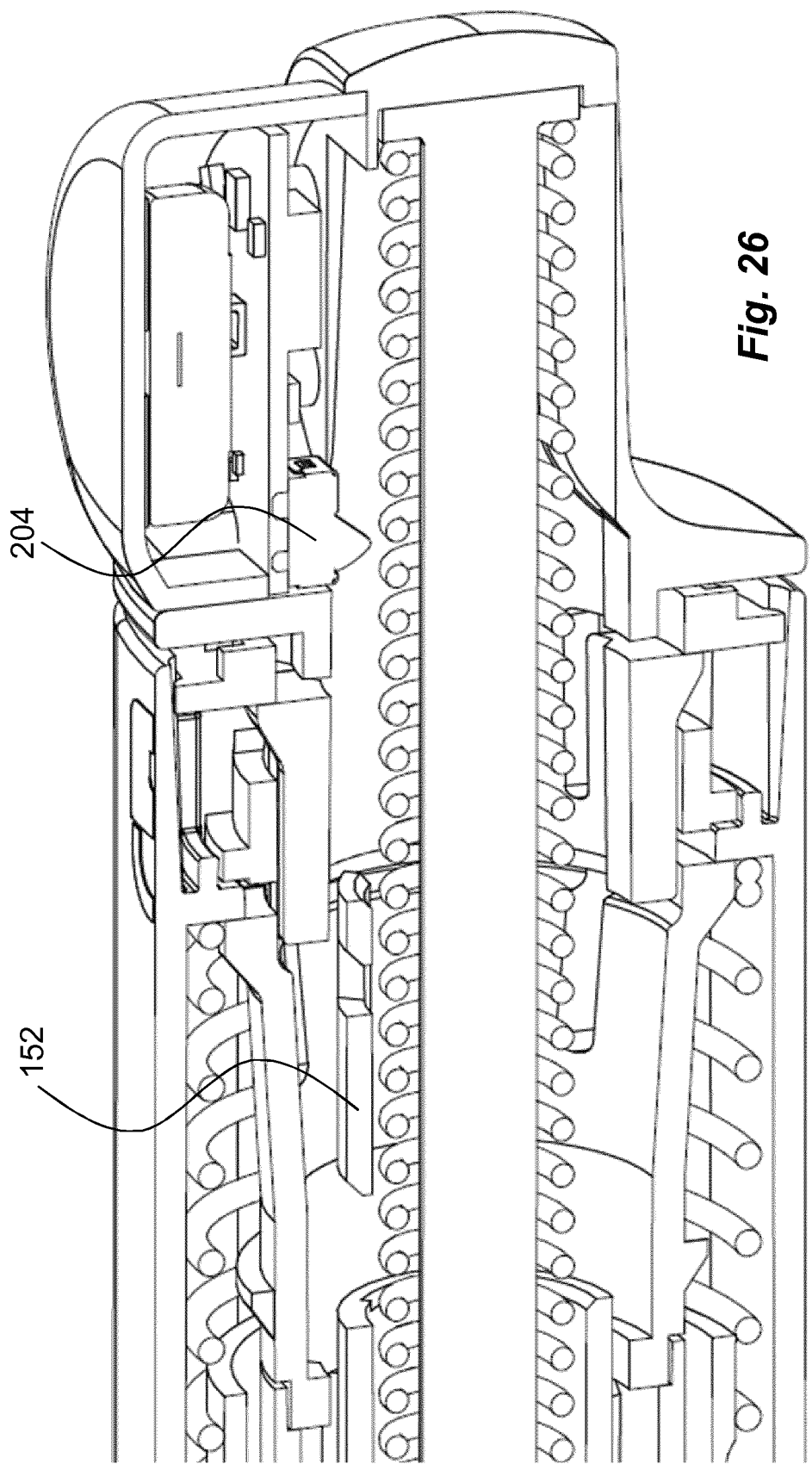
FIG. 26 is a functional view of the medicament delivery device of FIG. 1 during a different functional stage.

The movement of the plunger rod 152 in the proximal direction will cause the activator element 204 to come out of contact with the plunger rod 152, FIG. 26, which again activates the electronics circuit 194 such that a timer is initiated. The timer is set to count a pre-determined period, which period corresponds to a time period when it is safe to remove the medicament delivery device. This period could be based on the time it takes for the medicament delivery device to deliver the dose of medicament and possibly together with a period to stabilize the delivery in order to avoid medicament drooling from the injection needle. The end of the time period may be indicated to the user in an appropriate way. For example if lights are used, it may indicate red during the time period, switching to green when the time period has ended and that it is safe to remove the medicament delivery device.

When now the medicament delivery device is removed from the delivery site, the medicament delivery member guard 102 is again moved proximally to its extended position by the medicament delivery member guard spring 119, covering the needle 62. Now when the medicament delivery member guard 102 and its medicament delivery member guard extension 112 is moving proximally, the protrusions 118 of the medicament delivery member guard extension 112 will move longitudinally in relation to the rotator until the protrusions 118 come in contact with the wedge-shaped ledges 126 of the arms 124 of the rotator 122, pushing the arms 124 radially inwards so that the protrusions 118 pass, FIG. 26. Thereafter, the arms 124 will flex back, whereby the wedge-shaped ledges 126 will act as stops against the medicament delivery member guard 102 being moved distally, i.e. locking the medicament delivery member guard 102 in the extended, protecting position.

After use of the medicament delivery device, the recording unit may be utilized to perform a number of actions. For instance, the electronics circuit may activate the communication unit for transferring data from the storage elements to external devices as described above.

It is to be understood that the embodiments described above and shown in the drawings are to be regarded only as non-limiting examples of the disclosure and that it may be modified in many ways within the scope of the patent claims.

The invention claimed is:
1. A medicament delivery device comprising:
  a housing configured to accommodate a medicament container filled with medicament;
  a drive unit comprising a plunger rod operable to act on the medicament container;
  a manually operated actuator that, when operated, alters the drive unit from a locked state to a release state;
  a mechanical activation mechanism configured to interact with the drive unit and wherein said mechanical activation mechanism is movable between certain predetermined states when interacting with the drive unit;
  a recording unit capable of recording status changes of said medicament delivery device including the status of the mechanical activation mechanism;

detection elements operably connected to said recording unit and positioned such as to detect when the activation mechanism has been moved between certain predetermined states;

a medicament delivery member assembly operably attached to said medicament container for performing a priming operation of the medicament container; and a medicament delivery member guard movably arranged in said housing between a retracted position and an extended position covering said medicament delivery member after said priming operation, wherein, in the release state, the plunger rod of the drive unit is released and moved to exert a pressure on the medicament inside said medicament container, and wherein said detection elements are arranged to detect the movement of said plunger rod, wherein said recording unit further comprises (i) orientation elements capable of detecting angular positions of the medicament delivery device after activation, wherein said orientation elements are activated by the detection elements detecting movement of said plunger rod, and (ii) information elements capable of providing a user with information regarding correct angular positions of the medicament delivery device for the priming operation, and wherein said information elements are capable of providing the user with information regarding erroneous angular positions of the medicament delivery device for the priming operation.

2. The medicament delivery device according to claim 1, wherein said mechanical activation mechanism comprises a section of the plunger rod.

3. The medicament delivery device according to claim 1, wherein said information elements comprise any or combinations of light emitting elements, sound emitting elements, vibration emitting elements, visual display elements.

4. The medicament delivery device according to claim 1, wherein said plunger rod is moved during priming, which movement is detected by said detection elements, whereby the recording unit switches off said orientation elements.

5. The medicament delivery device according to claim 1, wherein said medicament delivery member guard is movable from the extended position to the retracted position during a penetration operation at a dose delivery site, that said medicament delivery member guard is operably connected to said drive unit wherein said medicament delivery member guard releases said plunger rod in the retracted position, causing a dose of medicament to be delivered through said medicament delivery member, wherein said detection elements are arranged to detect when said plunger rod has been released.

6. The medicament delivery device according claim 5, wherein said recording unit comprises a timer that is activated when said plunger rod has been released.

7. The medicament delivery device according to claim 6, wherein said recording unit activates said information elements when said timer has counted a pre-set time period to indicate that the medicament delivery device can be removed from the dose delivery site.

8. The medicament delivery device according to claim 1, wherein the recording unit further comprises a micro control unit programmed to handle data obtained from the detection elements and to provide information via the information elements.

9. The medicament delivery device according to claim 1, wherein the recording unit further comprising data storage elements.

10. A medicament delivery device comprising:

a housing configured to accommodate a medicament container filled with medicament;

a drive unit comprising a plunger rod operable to act on the medicament container;

a manually operated actuator that, when operated, alters the drive unit from a locked state to a release state;

a mechanical activation mechanism configured to interact with the drive unit and wherein said mechanical activation mechanism is movable between certain predetermined states when interacting with the drive unit;

a recording unit capable of recording status changes of said medicament delivery device including the status of the mechanical activation mechanism;

detection elements operably connected to said recording unit and positioned such as to detect when the activation mechanism has been moved between certain predetermined states; and a medicament delivery member assembly operably attached to said medicament container for performing a priming operation of the medicament container, wherein, in the release state, the plunger rod of the drive unit is released and moved to exert a pressure on the medicament inside said medicament container, and wherein said detection elements are arranged to detect the movement of said plunger rod, wherein said recording unit further comprises (i) orientation elements capable of detecting angular positions of the medicament delivery device after activation, wherein said orientation elements are activated by the detection elements detecting movement of said plunger rod, and (ii) information elements capable of providing a user with information regarding correct angular positions of the medicament delivery device for the priming operation, wherein said information elements are capable of providing the user with information regarding erroneous angular positions of the medicament delivery device for the priming operation, and wherein said plunger rod is moved during priming, which movement is detected by said detection elements, whereby the recording unit switches off said orientation elements.

* * * * *